US006727691B2

(12) United States Patent
Goldfine et al.

(10) Patent No.: US 6,727,691 B2
(45) Date of Patent: Apr. 27, 2004

(54) HIGH RESOLUTION INDUCTIVE SENSOR ARRAYS FOR MATERIAL AND DEFECT CHARACTERIZATION OF WELDS

(75) Inventors: Neil J. Goldfine, Newton, MA (US); Vladimir A. Zilberstein, Chestnut Hill, MA (US); Darrell E. Schlicker, Watertown, MA (US); David C. Grundy, Reading, MA (US); Ian Shay, Cambridge, MA (US); Andrew P. Washabaugh, Chula Vista, CA (US)

(73) Assignee: Jentek Sensors, Inc., Waltham, MA (US)

( * ) Notice: Subject to any disclaimer, the term of this patent is extended or adjusted under 35 U.S.C. 154(b) by 0 days.

(21) Appl. No.: 10/046,925

(22) Filed: Jan. 15, 2002

(65) Prior Publication Data

US 2002/0105325 A1 Aug. 8, 2002

Related U.S. Application Data

(63) Continuation-in-part of application No. 09/891,091, filed on Jun. 25, 2001, now abandoned.
(60) Provisional application No. 60/214,177, filed on Jun. 26, 2000, provisional application No. 60/248,104, filed on Nov. 13, 2000, provisional application No. 60/276,997, filed on Mar. 19, 2001, provisional application No. 60/277,532, filed on Mar. 21, 2001, provisional application No. 60/284,972, filed on Apr. 19, 2001, and provisional application No. 60/297,926, filed on Jun. 13, 2001.

(51) Int. Cl.[7] .................. G01B 33/12; G01N 27/90
(52) U.S. Cl. .................. 324/240; 324/226; 324/242; 228/102

(58) Field of Search .................. 324/240, 242, 324/243, 236, 237, 238, 293, 262, 226, 228; 228/102, 103, 104

(56) References Cited

U.S. PATENT DOCUMENTS

| | | | |
|---|---|---|---|
| 4,441,010 A | 4/1984 | Cornu et al. | 219/124.34 |
| 5,015,951 A | 5/1991 | Melcher | 324/232 |
| 5,047,719 A | 9/1991 | Johnson et al. | 324/242 |
| 5,146,163 A | 9/1992 | Nawa | 324/232 |
| 5,182,513 A | 1/1993 | Young et al. | 324/232 |
| 5,262,722 A | 11/1993 | Hedengren et al. | 324/242 |
| 5,389,876 A | 2/1995 | Hedengren et al. | 324/242 |
| 5,453,689 A | 9/1995 | Goldfine et al. | 324/239 |
| 5,463,201 A | 10/1995 | Hedengren et al. | 219/121.83 |
| 5,592,078 A | 1/1997 | Giragosian et al. | 324/207.18 |
| 5,793,206 A | 8/1998 | Goldfine et al. | 324/242 |
| RE36,986 E | 12/2000 | Melcher, deceased | 324/232 |
| 6,168,066 B1 * | 1/2001 | Arbegast | 228/102 |

* cited by examiner

Primary Examiner—Walter E. Snow
(74) Attorney, Agent, or Firm—Hamilton, Brook, Smith & Reynolds, PC

(57) ABSTRACT

A sensor that characterizes welds in materials. The sensor includes a meandering drive winding with at least three extended portions and at least one sensing element placed between an adjacent pair of extended portions. A time varying electric current is passed through the extended portions to form a magnetic field. The sensor is placed in proximity to the test material and translated over the weld region. An electrical property of the weld region is measured for each sensing element location. The weld quality is determined using a feature of the electrical property measurement and location.

44 Claims, 32 Drawing Sheets

HIGH RESOLUTION INDUCTIVE SENSOR ARRAYS FOR MATERIAL AND DEFECT CHARACTERIZATION OF WELDS

RELATED APPLICATION(S)

This application is a continuation-in-part of U.S. application Ser. No. 09/891,091, filed Jun. 25, 2001 ABN, which claims the benefit of U.S. Provisional Application No. 60/214,177, filed Jun. 26, 2000, U.S. Provisional Application No. 60/248,104, filed Nov. 13, 2000, U.S. Provisional Application No. 60/276,997, filed Mar. 19, 2001, U.S. Provisional Application No. 60/277,532, filed Mar. 21, 2001, U.S. Provisional Application No. 60/284,972, filed Apr. 19, 2001, and U.S. Provisional Application No. 60/297,926, filed Jun. 13, 2001. The entire teachings of the above applications are incorporated herein by reference.

BACKGROUND

The technical field of this invention is that of nondestructive materials characterization, particularly as it applies to postweld and in-process weld scanning for quality control, in-process monitoring, and seam tracking using spatially periodic field eddy current sensors.

There is an increasing need for a nondestructive method for assessing the quality of welds between materials, including the detection and characterization of defects. In particular, friction stir welding is becoming more commonly used as a joining technique for a variety of metals, including aluminum, titanium and nickel base alloys as well as steels. The quality of the weld depends upon a variety of factors, including the materials, the rotation rate, feed, positioning, applied pressure from the pin tool, and the penetration ligament. Defects such as cracks, lack of penetration (LOP), and lack of fusion can compromise the integrity of the joint and can lead to component failure.

Weld examinations are currently performed to characterize quality of the welds, qualify a welding procedure or qualify welders. These examinations are performed to detect cracks, lack of fusion, lack of penetration, areas of excessive porosity, or unacceptably large inclusions. Liquid penetrant inspection (LPI) is widely used for detection of surface-connected defects in welded components fabricated from nonmagnetizable materials. In some cases, LPI fails to detect these surface-connected defects, such as in the case of tight cracks, cracks densely filled with foreign matter, or weakly-bonded LOP defects in friction stir welds (FSWs).

For components fabricated from magnetizable materials, such as carbon and low-alloy steels, magnetic particle inspection (MPI) is typically used for detection of surface-connected cracks. Some MPI techniques are claimed to detect cracks that are masked by smeared metal so that the cracks are not directly exposed to the surface. Furthermore, MPI is permitted for inspection through thin coatings typically less than 0.003 in. (0.075 mm) thick. However, MPI is limited in crack detection capability and, for coated surfaces, may require coating removal. Methods are needed to inspect carbon and low-alloy steel components for cracks that are below the MPI detection threshold and for inspections that do not require coating removal. There is also a need to characterize residual stresses in these welds. Other conventional nondestructive testing methods such as conventional eddy current sensing are limited in their sensitivity to small flaws in welds and in their capability to extract spatial information about changes in the weld microstructure and flaw characteristics. The use of conventional eddy current sensing often involves extensive scanning along and across the weld.

Etching with a variety of metallographic etchants is also used to reveal macrostructural or microstructural characteristics of welded joints, including weld metal, heat-affected zone, and base metal. In the case of FSW, which is joining by plastic deformation and stirring below solidus, etching can reveal the dynamically recrystallized zone (DXZ), thermomechanically affected zone (TMZ), heat-affected zone (HAZ) and base metal. Etching of FSWs can also be used as a method for characterizing LOP defects, by revealing the relevant width of the DXZ. For example, as shown in FIG. 1, the DXZ, TMZ and HAZ show up after etching as distinctly different zones permitting direct measurement of the width of the DXZ that has penetrated to the backside of the welded panels. Etching of panels joined by FSW would, in the case of butt welds, reveal these zones on both the front and back sides. Unfortunately, the etching process is time consuming, not practical for inspection of long welds required for large structures, such as spacecraft and aircraft, not environmentally friendly, and often not permitted in production. Methods are needed to inspect these surfaces rapidly and nondestructively.

It is often critical to characterize microstructural variations of metal products such as ingots, castings, forgings, rolled products, drawn products, extruded products, etc. Etching of selected samples is used for this purpose but is not practical or permissible for large surfaces or statistically significant quantities, areas, or lengths. It is definitely not acceptable for 100 percent inspection of these products when information on microstructural variations, including imaging of these variations and their quantitative characterization, is required over the entire surface of a product. Furthermore, etching of large surfaces in components that are suspected to contain local zones that are different due to fabrication problems, service-induced or accident-induced effects is not practical, unless the locations of such zones are known a priori.

SUMMARY

The use of eddy current sensors and high resolution conformable eddy current sensor arrays permits quality control monitoring for fusion welds, friction stir welds (FSWs), metal products such as ingots, castings, forgings, rolled products, drawn products, extruded products, etc., and components with locally different microstructures. In one embodiment, the quality of the joint or weld is determined from eddy current measurements of the test material properties across the weld region by determining a feature of the weld from a combination of the electrical property measurement and the location information. In an embodiment, the electrical property of the test material used to determine the feature is the electrical conductivity. In one embodiment, the feature is the width of the dynamically recrystallized zone (DXZ). Descriptions for FSWs may also be applied to other weld methods.

In another embodiment, friction stir welds are characterized by eddy current sensors and sensor arrays having a meandering drive winding with extended portions for imposing a magnetic field. In another embodiment, the drive winding forms a modified meandering pattern that approximates a periodic field as described in patent application No. 60/276,997, filed Mar. 19, 2001, the entire teachings of which are incorporated herein by reference. The windings can be fabricated onto rigid or conformable substrates. Sensing elements placed between the extended portions of the drive winding respond to the properties of the test material. A single sensing element can be placed between each pair of extended portions and electrically connected to each other sensing element to provide a single output response for the sensing when scanned over the test material. Alternatively, numerous sensing elements can be placed in rows parallel to the extended portions. This facilitates imaging of the material properties, particularly when the sensor array is scanned in a direction perpendicular to the row of sensing elements. In one embodiment, the sensing elements are coils that couple to the drive windings through induction and the sensing windings have dimensions small enough to provide imaging resolution suitable for measuring the width of the weld region at or near the surface, e.g., at the crown or root of a fusion weld or DXZ that penetrates through the plates joined by FSW. In a second embodiment, the sensing elements incorporate magnetoresistive sensors to permit inspection down to low frequencies (such as a 50 Hz or even dc) for characterization of relatively thick plates, such as 0.5 in. (12.5 mm) aluminum lithium alloy plates. In one embodiment, the sensor construct uses a circular or rectangular distributed drive winding that excites a smoothly varying shaped magnetic field. In a particular embodiment, the magnetoresistive elements are giant magnetoresistive sensors.

Scanning of the sensors over the weld region permits the quality of the weld to be determined through features of the electrical property profile across the weld. The orientation of the sensor, relative to the weld axis, can be varied to adjust the sensitivity to the different types of defects, such as intermittent planar flaws, lack of penetration (LOP) of the tool tip, and weak metallurgical bonds. When deep penetration is used, other defects such as porosity, internal flaws, cracks, and weak bonds are imaged or detected. This can apply to butt joints, lap joints, or other weld geometries. In one embodiment, the extended portions of the sensor are oriented parallel to the weld axis. In another, the extended portions are oriented perpendicular to the weld axis. With each orientation, the sensor can be scanned across the weld, perpendicular to the weld axis, or along the weld, parallel to the weld axis. Scanning the sensor along a path that forms a small angle, such as 15 degree, with the weld axis, with the extended portions oriented perpendicular to the translation path, provides measurement sensitivity to both longitudinal and transverse flaws.

For the features used in determining the weld quality, in one embodiment the electrical property is the electrical conductivity. In another embodiment, the electrical property is the magnetic permeability. In another embodiment, the feature is the width of the weld at different depths determined using multiple frequency measurements. The weld quality could then be indicated by the LOP thickness or the presence of planar flaws. In another embodiment, the weld quality feature is obtained from images of the electrical property variations over the region of the weld. Again, in this case, the quality of the weld can be indicated by the presence of planar flaws, weak bonds, or other defects.

The frequency of the excitation also influences the measurement response and can be used to determine the quality of the weld. In one embodiment, a single high frequency measurement is made of conductivity and proximity at each sensing element to measure only the near surface properties of the material. In another embodiment, multiple frequencies are used to determine the variation of material properties with depth from the surface. This includes the generation of three-dimensional images of FSW, including the weld nugget or DXZ, using model based methods that model the magnetic field interactions with the nugget; these methods can be either analytical or numerical, such as finite element methods. In one embodiment, the model is used to generate two-dimensional measurement grids and higher-order multi-dimensional databases, respectively, of sensor responses to FSW zones, including the DXZ, property variations. In one example, the estimated properties of the DXZ are the width of the penetration zone at the base of the weld and the width of the DXZ at a selected depth from the base of the weld. In another example, the material properties are the conductivity of the LOP region and the thickness of the LOP defect thickness. The multiple frequency imaging method is then used to estimate these two parameters using a combination of measurement grid table look-ups, intelligent root searching methods, or apriori knowledge of the nugget geometry to estimate nugget geometry parameters. The frequency can range from 100 Hz to 10 MHz. In another embodiment, dissimilar welds are inspected and the shape of the electrical conductivity response determines the weld quality. A good weld has a gradual transition while a bad weld has a more abrupt transition between the plates for a butt weld.

In another embodiment, a sensor array is used to characterize subsurface features such as porosity, cracks, lack of fusion, material condition and properties before and after heat treatment (or other processes), as well as other material anomalies or property distributions that affect metal product, component, or weld quality. In another embodiment high frequencies (100 kHz to 10 MHz) are used to detect surface breaking flaws as an automated replacement for liquid penetrant testing.

In another embodiment, the sensing elements include magnetoresistive sensors. Similar to the inductive coils, images of the material properties can be obtained by scanning rows of magnetoresisitive elements oriented parallel to the extended portions of the drive winding. This image can be formed from the electrical property measurements across and along the weld region. In an embodiment, the weld quality is indicated by the surface and through thickness properties of the weld region. The weld quality can be indicated by the presence of a crack-like defect, an LOP defect, the presence of an internal flaw, or a weak metallurgical bond. In another embodiment, an LOP defect can be detected by scanning the sensor over the top surface such that the LOP defect is on the opposite side of the weld. The magnetoresistive sensing elements may further comprise encircling secondary coils to improve the dynamic range of the measurements and bias the magnetoresistive sensors, as described in patent application Ser. No. 10/045,650 filed Nov. 8, 2001, entititled "Deep Penetration Magnetoquasistatic Arrays," by Sheiretov et al., Attorney Docket No. 1884.2007-001, the entire teachings of which are incorporated herein by reference. This provides a potential replacement for radiography or phased array ultrasonics for thick plate (0.25 to 1 inch thick) inspections. The secondary coils can be used in a feedback configuration with external electronic circuitry to maintain the field in the vicinity of the magnetoresistive element.

For magnetizable metal products, components, and welds, such as carbon and high-strength low-alloy steels, the magnetoresistive sensing element arrays are used to measure from DC to high frequencies and map residual stress patterns and the geometry of the weld regions. In one embodiment, scans are made with both inductive sensing elements and magnetoresistive sensing elements to provide inspections from DC up to high frequencies (such as 10 MHz). For these materials, the high resolution imaging with conformable eddy current sensor arrays that use a single wavelength drive winding with an array of sensing elements is a direct replacement for magnetic particle inspection and does not require paint removal. In another embodiment, multiple frequencies are used to measure the depth of cracks that are either surface breaking of subsurface. In one embodiment the bi-directional permeability is related to weld residual stress and heat affected zone residual stresses.

In an embodiment, the eddy current sensors and eddy current sensor arrays having drive windings with extended portions can also be used for the quality control of joining processes. In one embodiment, the joining process involves tracking, such as locating or following, the seam between the joined materials. Furthermore, varying the orientation of the extended portions with respect to the seam axis also provides information about the seam orientation. In an embodiment, the electrical property of the measurement is the electrical conductivity. In another embodiment, the joining process is a friction stir welding process. One embodiment further comprises mounting the sensor in the anvil to monitor the weld process beneath the welding tool. Another embodiment comprises mounting sensors ahead of and behind the anvil on the opposite side as the weld. Another embodiment comprises mounting sensors ahead of and behind the welding tool on the same side as the weld.

In another embodiment, a sensor is used to control the tool and the position of the sensor with respect to the tool position is kept constant. This configuration can be applied to a fixed material with the tool moving or a fixed tool position with the material moved past the tool. In one embodiment, a sensor is placed over the front surface of the material. In another embodiment, another sensor is placed behind the test material for monitoring the weld processes on the surface opposite the weld tool. In each of these cases, a preferred embodiment has the sensors not in contact with the test material.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
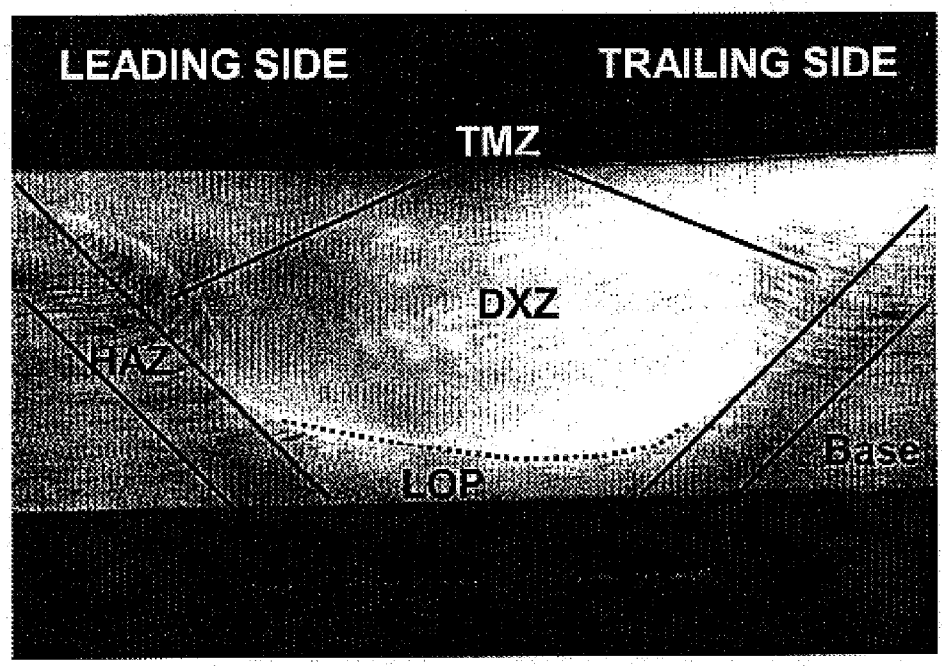
FIG. 1 shows a cross-section of a friction stir weld with lack-of-penetration defect in Al—Li alloy plate.

The use of single element sensors and high resolution conformable eddy current sensor arrays is described for quality assessment and manufacturing control of fusion welds, FSWs, metal products such as ingots, castings, forgings, rolled products, drawn products, extruded products, etc., and components with locally different microstructures. A representative photomicrograph of weld joint, in this case FSW, is shown in FIG. 1. Friction stir welding is a solid-state joining process. The formation of an FSW is characterized by complex metal flow patterns and microstructural changes. For aluminum alloys, three distinctly different major zones can be typically identified as: (1) a dynamically recrystallized zone (DXZ), or weld nugget, (2) a thermomechanical or heat- and deformation-affected zone (TMZ or TMAZ), adjacent to the weld nugget on both leading and trailing sides of the joint, and (3) a heat-affected zone (HAZ) (Arbegast, 1998; Ditzel, 1997). The HAZ includes material that has been exposed to a thermal cycle which modifies the microstructure and/or mechanical properties but does not involve plastic deformation. The TMZ and DXZ includes material that has been plastically deformed by the FSW tool, but the DXZ has a different microstructure than the nonrecrystallized TMZ. For materials other than aluminum alloys, the entire TMZ region may appear to be recrystallized so that a distinct DXZ region separate from the TMZ is absent. Consequently, methods for characterizing the weld quality based, for example, on the width of the DXZ in aluminum alloys can be extended to be based on the width of the TMZ for other materials.

Compared to conventional fusion welds, friction stir welds are known to contain very few types of defects. The two types of defects that have been noted in friction stir welds are: (1) tunnel defects within the nugget and (2) lack of penetration (LOP) (Arbegast, 1998). LOP exists when the DXZ does not reach the backside of the weld due to inadequate penetration of the pin tool. The LOP zone may also contain a well-defined cracklike flaw such as a cold lap, which is formed by distorted but not bonded original faying, i.e., butt, surfaces. This occurs as a result of insufficient heat, pressure and deformation. However, the LOP can be free of well-defined cracklike flaws, yet not be transformed by the dynamic recrystallization mechanism since temperatures and deformation in the LOP may not be high enough. Although it may contain a tight "kissing bond," this second type of LOP defect is the most difficult to detect with alternative methods such as phased-array ultrasonic or liquid penetrant inspection. The MWM-Array methods described here offer the potential to reliably detect and quantitatively characterize both types of LOP defects.

Figure 2:
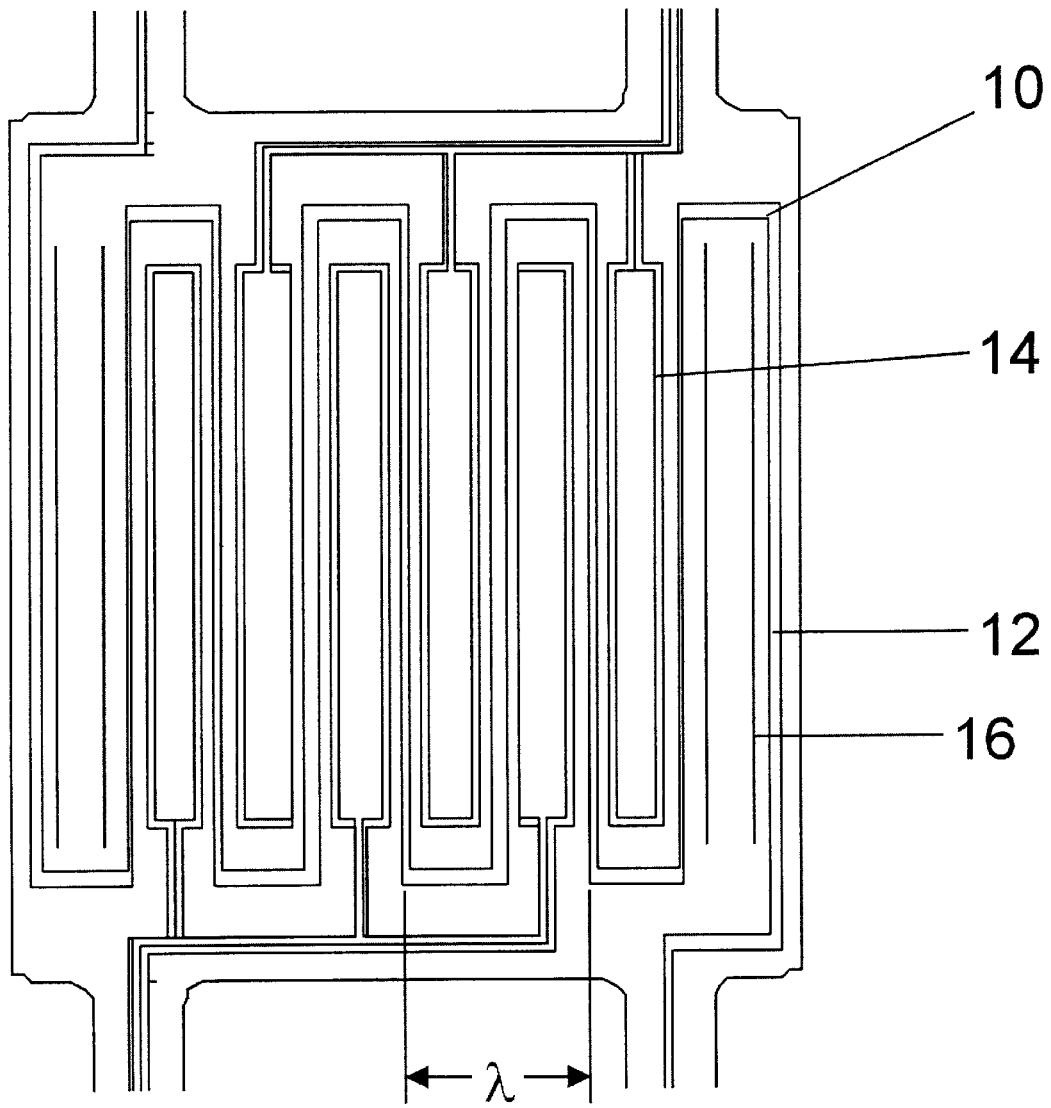
FIG. 2 shows a plan view for an MWM sensor.

In one embodiment, eddy current sensors comprised of at least one meandering drive winding and multiple sensing elements are used to inspect the region connecting joined materials. An example sensor is shown in FIG. 2, which shows the basic geometry for a Meandering Winding Magnetometer (MWM™) sensor. The sensor comprises a meandering primary winding 10 having extended portions 12 for creating the magnetic field and secondary windings 14 within the primary winding for sensing the response of the material under test (MUT). The primary winding is fabricated in a square wave pattern with the dimension of the spatial periodicity termed the spatial wavelength $\lambda$. A current is applied to the primary winding and a voltage is measured at the terminals of the secondary windings. The magnetic vector potential produced by the current in the primary can be accurately modeled as a Fourier series summation of spatial sinusoids, with the dominant mode having the spatial wavelength $\lambda$. The sensing elements can be connected in series to form a single "sense" output signal or individual connections can be made to each element to form an array of "sense" output signals. Passive, dummy, conductors 16 help to maintain the periodicity of the conductor pattern and the magnetic field.

This MWM sensor and MWM-Array sensors have a demonstrated capability to independently measure proximity and material properties as described in U.S. Pat. Nos. 5,015,951, 5,453,689, and 5,793,206, the entire teachings of which are incorporated herein by reference. The MWM is a "planar" eddy current sensor that was designed to support quantitative and autonomous data interpretation methods. These methods, called grid measurement methods, permit crack detection on curved surfaces without the use of crack standards, provide quantitative images of absolute electrical properties (conductivity and permeability) and permit determination of coating thickness, as well as characterization of process-affected layers, without requiring field reference standards (i.e., calibration is performed in air away from conducting surfaces). The sensors are microfabricated onto a substrate that is typically flexible to provide conformability with curved surfaces; for some applications, the substrate can be rigid or semirigid. The meandering primary windings may be formed by a single conducting element or by a series of adjacent loops, as described in U.S. patent application Ser. No. 09/666,524, filed on Sep. 20, 2000, the entire teachings of which are incorporated herein by reference.

Figure 3:
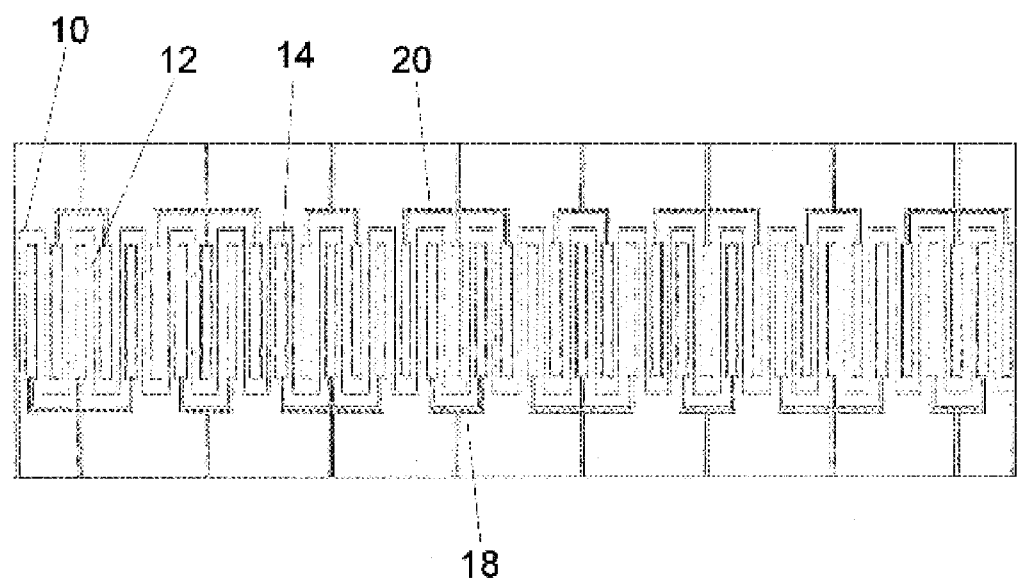
FIG. 3 shows a plan view of an MWM-Array.
Figure 4:
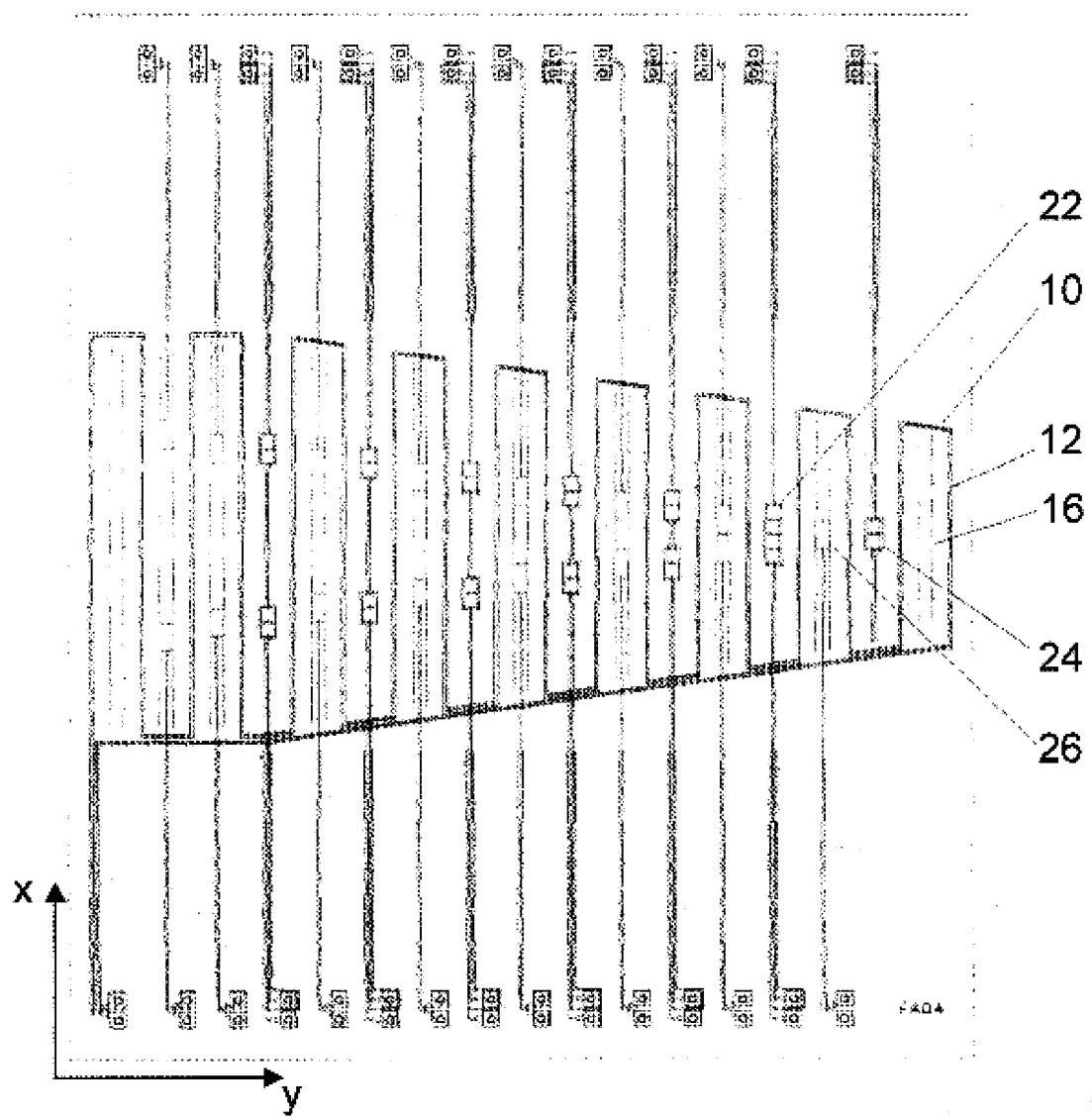
FIG. 4 shows a plan view of an MWM-Array having a tapered primary winding.

FIG. 3 and FIG. 4 show schematics for two MWM-Arrays. Each array has a single primary winding 10 containing extended portions 12 and multiple secondary or sensing elements (14 in FIGS. 3 and 22 in FIG. 4) to permit property images when scanned over a surface. The responses from individual or combinations of the secondary windings can be used to provide a plurality of sense signals for a single primary winding construct as described in U.S. Pat. No. 5,793,206, the entire teachings of which are incorporated herein by reference. In FIG. 3, the sensing elements of the array comprise the combinations of two secondary elements 18 or three secondary elements 20. These sensing elements can also be combined together on an electronic circuit board, away from the surface of the sensor, so that each sensing element pixel contains a group of five secondary elements.

The winding geometry for the MWM makes the response dependent upon the orientation of the sensor with respect to the defect being detected. For example, the eddy currents induced in the material under test (MUT) flow in a plane parallel to the plane of the MWM windings and a direction parallel to the extended portions 12 of the primary winding meanders. Cracks that are perpendicular to the extended portions of the primary winding meanders then interrupt the current path, leading to a decrease in the effective MUT conductivity. In contrast, cracks that are parallel to the extended portions of the primary winding meanders and do not extend beyond the primary winding do not interrupt the induced eddy currents appreciably and the MWM response to cracks in this orientation is diminished. Possible cracklike flaws associated with FSWs include unbonded original butt surfaces either within large LOP or, in the case of a large off-center tool position, outside the lower portion of the joint.

In the format of FIG. 3, the sensing elements 14 provide absolute measurements of the material response. In the tapered winding format of FIG. 4, the sensing elements 22 are configured for both absolute measurements 26 and differential measurements 24. In each array, current flow through the primary winding creates a spatially periodic magnetic field that can be accurately modeled. The voltage induced in the secondary elements by the magnetic field is related to the physical properties and proximity to the MUT. In the format of FIG. 3, a single sensing element is located within each meander of the primary winding and each grouping of interconnected sensing elements 20 provides an image pixel. Scanning of the array over an MUT then provides an image of the material properties. In the tapered format of FIG. 4, except for the rightmost elements, two sensing elements (either absolute or differential) are located within each meander of the primary winding. The sensing elements are offset in the x direction to provide an overlap and complete coverage of the MUT when the array is scanned in the y direction. Using multiple sensing elements within the array with parallel data acquisition instrumentation, as opposed to multiplexed instrumentation, improves data rates and provides real-time imaging capabilities. The use of multiple sensing elements with one meandering drive permits high image resolution and sensitivity to local property variations. Furthermore, the energy in the imposed magnetic field decreases exponentially with distance into the MUT with a decay constant determined by both the spatial wavelength of the primary winding and the excitation frequency. Deep penetration of the magnetic fields into the MUT and sensitivity to relatively deep defects or material property variations is then accomplished with large wavelengths and low operating frequencies.

For the tapered format of FIG. 4, the combination of both differential and absolute sensing elements within the same footprint of a meandering primary winding provides new imaging capabilities. The differential elements 24 are sensitive to slight variations in the material properties, while the absolute elements 26 with the grid methods provide robust imaging of absolute conductivity that is automatically compensated for local lift-off variations as each absolute sensing element is independent of the response of the other elements. The measured properties from each absolute sensing element can then be combined together to provide a two-dimensional mapping of the material properties. The differential sensor measurements can be combined with one, some, or all of the absolute measurements to provide other methods for creating two-dimensional mapping of the absolute material properties (including layer thicknesses, dimensions of an object being imaged, and/or other properties) and proximity. The property and proximity information obtained from the absolute measurements can be used as inputs for models that relate the differential response to absolute property variations. Filtering schemes can also be developed to combine the differential and absolute data to enhance image features of interest and increase flaw detection sensitivity.

Figure 5A:
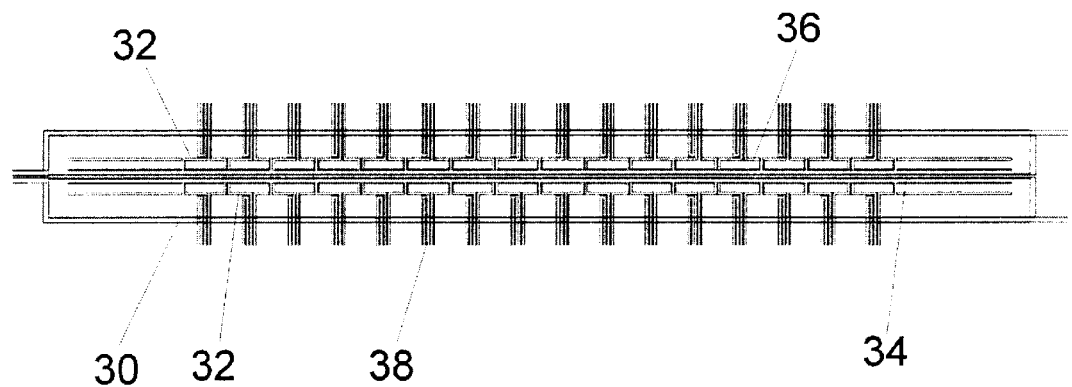
FIG. 5A shows a plan view of an MWM-Array having multiple elements within each meander and FIG. 5B shows the drive winding.

FIG. 5A shows another MWM-Array having two rows of sensing elements. This array only uses a single wavelength meandering primary winding and is described in detail in U.S. Provisional Application No. 60/276,997, submitted Mar. 19, 2001, the entire contents of which are incorporated herein by reference. The array comprises a pair of loops forming meander primary windings 30 (FIG. 5B) and rows of secondary elements 32 within each primary winding meander. Connections 38 are made to each sensing element 36 within each row 32. The sensor array is a layered structure with the central conductors for the primary winding 34 located in the same plane as the sense elements 36 and connections 38. The remaining primary winding conductors are located in a separate plane, behind the plane of the sense elements and separated from the sense elements by a layer of insulation. The use of multiple sensing elements within one or more meanders facilitates imaging of local property variations over wide areas as the array is scanned over the MUT in a direction perpendicular to the extended portions of the primary winding and the rows of sense elements.

Figure 5B:
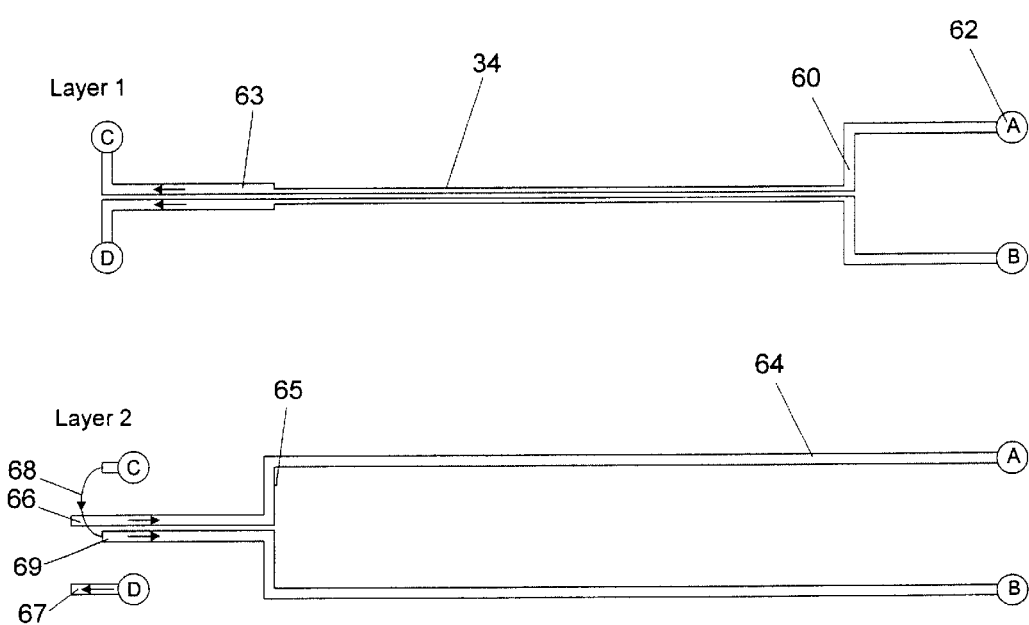

FIG. 5B shows a more detailed view of the primary winding. The central conductors 34 of the primary winding are in Layer 1. The central conductors are then connected to perpendicular conductors 60 that provide a boundary for the active area of the sensing structure and lead to vias 62 that provide pathways for connecting to Layer 2. The return conductors 64 for the primary winding are located in Layer 2 and connect to perpendicular conductors 65 that provide another boundary for the sensing structure. When fabricated, Layer 1 is placed over Layer 2 so that the via connections A, B, C, and D are vertically aligned. Except for the central conductors 34, the primary winding conductors 63 are made relatively wide to reduce the series resistance of the windings. The arrows indicate the current flow direction through the primary winding. Terminal connections to the primary winding are made to the conductors 66 and 67. The cross-connection 68 made between via C and the conductor 69 near the bond pads, which are not illustrated, maintain continuity of the current path.

Figure 6:
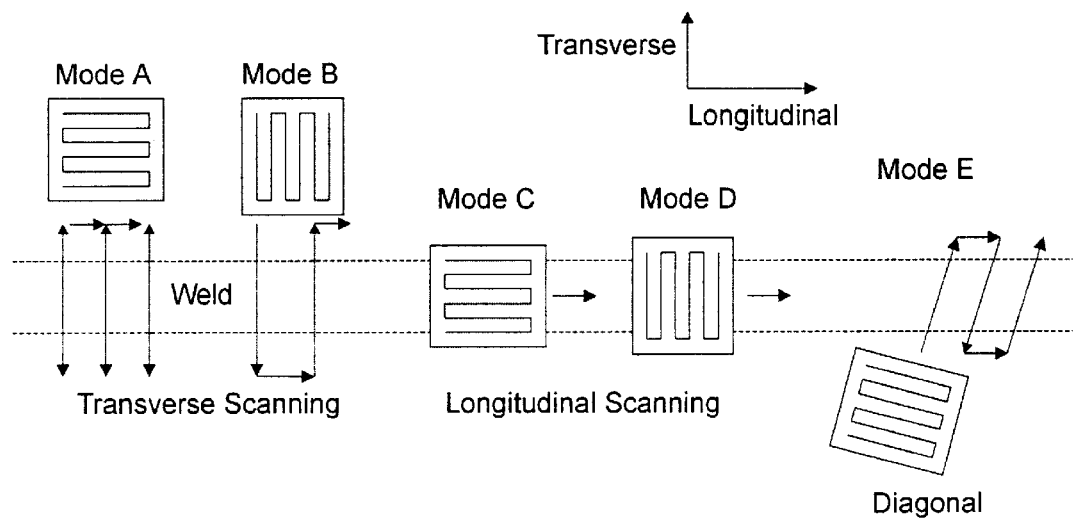
FIG. 6 shows scan orientations of the sensor for LOP and crack detection.

The different types of scanning modes for postweld inspection of FSWs, including the effects of sensor orientation with respect to the weld, are illustrated in FIG. 6. In Mode A, the extended portions (i.e., longer segments) of the primary winding are oriented parallel to the weld and the sensor is scanned across the weld in a transverse direction. In this orientation, MWM sensors and MWM-Arrays are sensitive to the material property variations associated with LOP but relatively insensitive to the presence of longitudinal planar flaws (such as cracks or cold laps). In Mode B, the longer segments of the primary winding are oriented perpendicular to the weld and scanned across the weld in the transverse direction. In this orientation, the MWM sensors and MWM-Array are highly sensitive to the presence of longitudinal planar flaws, such as cracks. For these transverse scanning modes, the transverse scans must be performed incrementally along the length of the weld to provide complete inspection coverage of the weld.

To increase the inspection speed along the weld, longitudinal scans can also be performed along the weld. In Mode C of FIG. 6, the longer segments of the primary winding are oriented parallel to the weld for LOP defect detection and sizing. In Mode D, the longer segments of the primary winding are oriented perpendicular to the weld for both LOP defect detection and sizing and crack detection. For the longitudinal scan modes, it is desirable, for complete coverage of the weld region, to have high resolution MWM-Arrays with multiple sensing elements spanning the weld region from the base metal on one side of the weld to the base metal on the other side of the weld. This facilitates the creation of two-dimensional images of the material property variations both across and along the weld. It is also possible to combine the advantages of both transverse and longitudinal scanning, as illustrated in Mode E of FIG. 6. For example, rotating the sensor so that the longer segments of the primary winding form a small angle with the weld axis, such as 15°, and scanning across the weld at an angle to the weld axis, such as 75°, can provide detailed images of the weld region and detect cracks in the same scan, albeit with some loss of sensitivity.

To demonstrate sensitivity to LOP defect presence and size, a variety of measurements were performed on several groups of FSW specimens; within each group the FSW panels were fabricated from the same combination of materials using the same procedure. In one group, measurements were performed on aluminum lithium specimens. Two of these specimens had no LOP defect, two had a 0.02-in. thick LOP defect, one had a 0.040-in. thick LOP defect, and one had a 0.090-in. thick LOP defect. Transverse scans were made across the welds at several locations along the weld at intervals of three inches.

Figure 7:
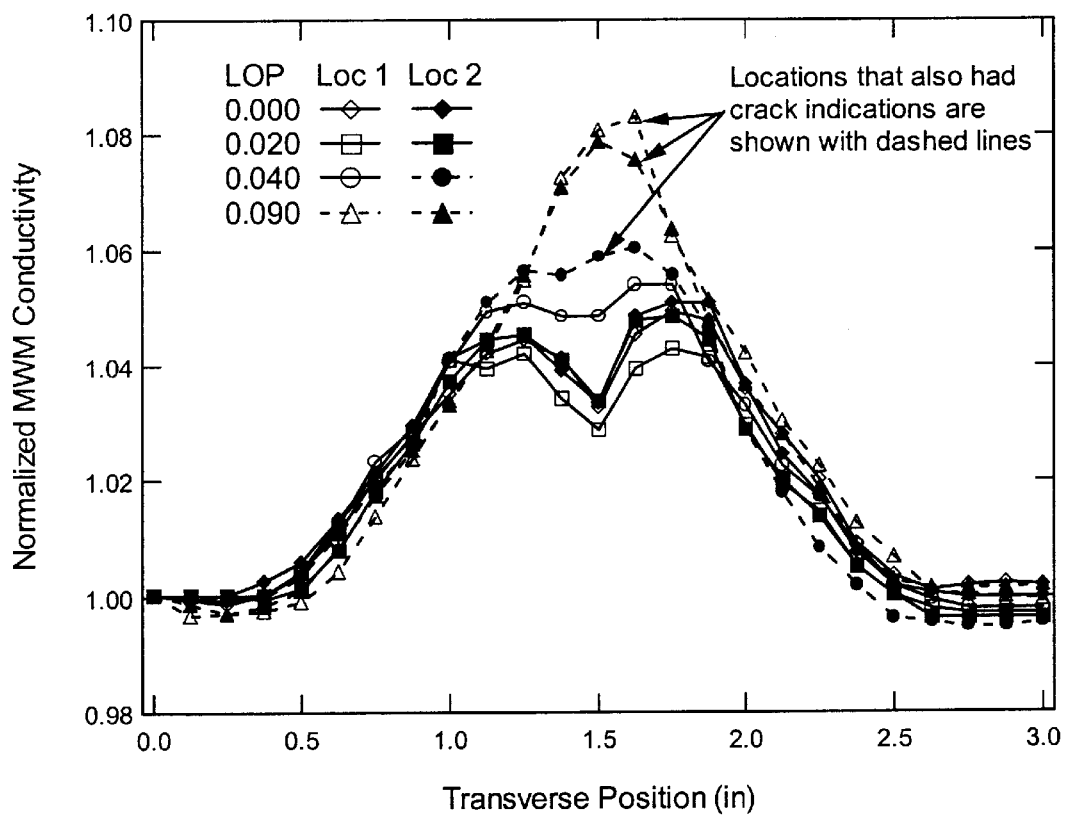
FIG. 7 is a plot of the normalized effective conductivity for similar metal FSW specimens with a single element MWM oriented parallel to the weld.

FIG. 7 shows plots of the normalized electrical conductivity for transverse scans across the back side of several of the FSW specimens from this first group. These scans correspond to Mode A of FIG. 6 and used the sensor illustrated in FIG. 2 which has all of the secondary windings connected together to form a single sense element. The sensor was manually scanned across the weld in 0.25 inch (6.35 mm) increments and used an excitation frequency of 250 kHz. The conductivity was normalized by dividing the measured effective conductivity by the measured conductivity of the base metal. The normalized conductivity increases in the HAZ but tends to decrease in the TMZ toward the DXZ at the center of the weld on the back side. The presence of LOP defects and cracks, which were detected more readily with scans using Mode B of FIG. 6 as described below, tend to increase the conductivity measured at the center of the weld in Mode A. These transverse scans, with the extended portions of the primary winding parallel to the weld, demonstrate sensitivity to the LOP defect presence and size. Note that in these samples the entire weld region was 2 inches (50.8 mm) wide and the sensor had a square footprint of approximately 0.5 inches (12.7 mm) on each edge. As a result, the response of the sensor is an averaged response over several of the weld zones illustrated in FIG. 1. Higher resolution sensor arrays, with sensing element dimensions comparable to or smaller than the FSW region thickness, can provide more accurate measurements of the local property variations in the FSW region.

Figure 8:
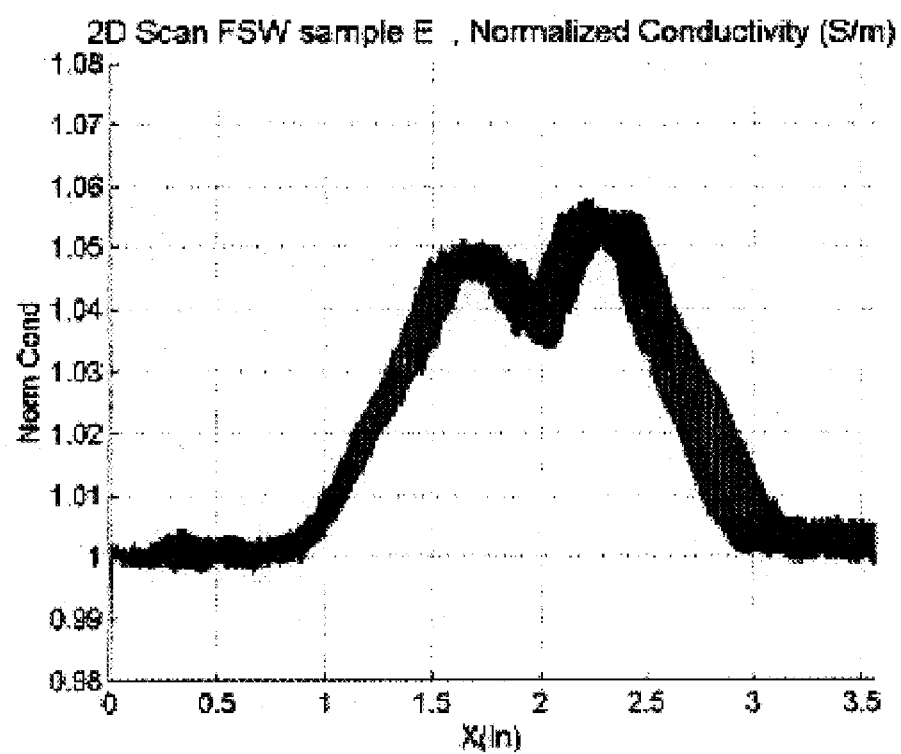
FIG. 8 is a plot of the normalized effective conductivity profile across a FSW for a similar metal FSW specimen with a single element MWM oriented parallel to the weld obtained from transverse scans with a position encoder at multiple longitudinal locations.

FIG. 8 provides a representative plot of the normalized effective conductivity in which a linear encoder provides the transverse location of the sensor. This allows continuous measurements to be taken during the scan and yields a higher resolution plot of the conductivity profile across the weld zone than is possible using manual scanning techniques. The conductivity profile was measured in 0.25 inch (6.35 mm) increments down the length of the weld and covered over an approximately 6-½ inch (0.17 m) long section of the weld. The variation in the conductivity along the weld at each transverse (X) position is indicated by the thickness of the conductivity profile plot line.

Figure 9:
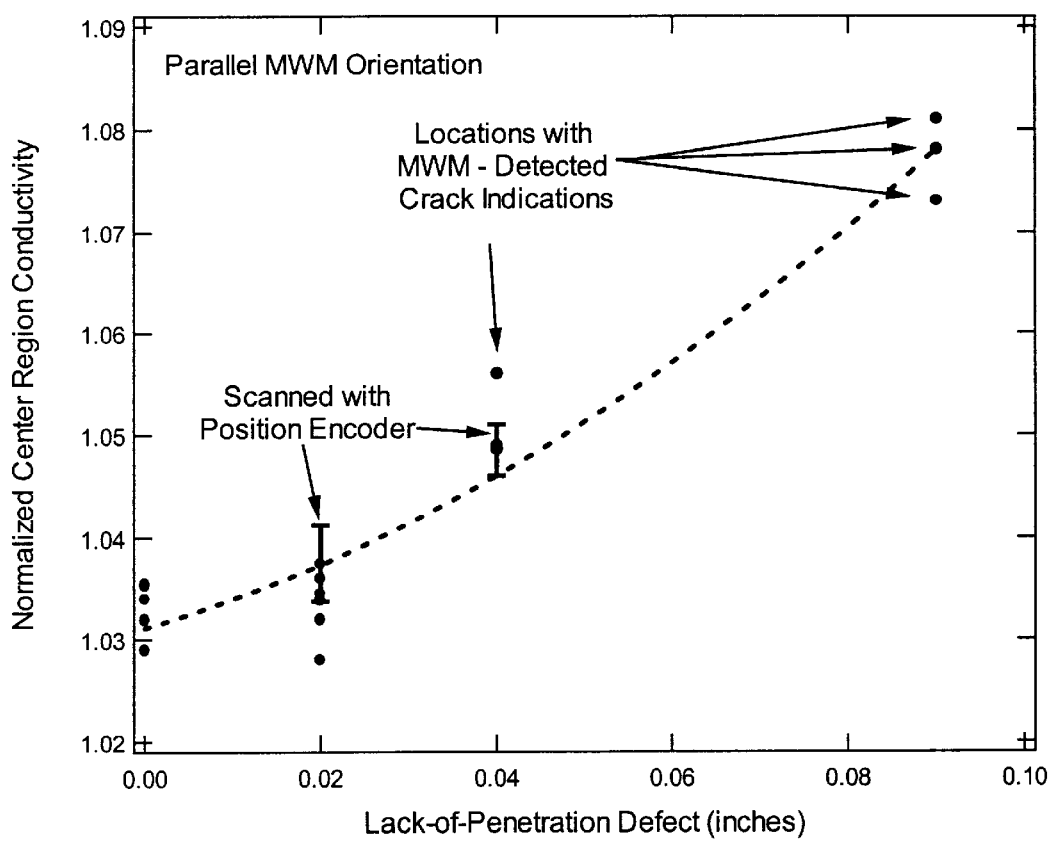
FIG. 9 is a plot of the correlation between the normalized center region effective conductivity as a function of the LOP thickness for similar metal FSWs fabricated using the same FSW procedure.

FIG. 9 shows a correlation between the normalized MWM conductivity in the center portion of the weld region with the LOP depth for FSW specimens fabricated according to the same procedure. The values plotted represent either the minimum in the center region "dip" or the maximum on the plot when no dip occurs for the data of FIG. 7 and FIG. 8. Note that the error bars shown for two of the specimens correspond to data obtained in a continuous scanning mode with a linear encoder indicating position along the scan. At the measurement frequency of 250 kHz and a base metal conductivity of approximately 11.6 MS/m (20% IACS), the sensing magnetic fields do not penetrate beyond the LOP defect. The sensitivity to LOP defect thickness is due to a correlation with microstructural changes that affect the near surface electrical conductivity within the first 0.01 inches. Available metallographic data for friction stir welds with a LOP suggest that the material in the LOP is partially deformed. Also, while the temperature and deformation within the LOP during friction stir welding are not high enough for dynamic recrystallization, the metal temperature is sufficiently high and time at temperature is sufficiently long to influence precipitate morphologies (Mahoney, 1998). The near-surface size and distribution of precipitates in the LOP zone depends on the thickness of the LOP defect (or, more accurately, on the distance from the weld nugget) since the local nucleation, growth, and coarsening of precipitates are a function of temperature and time at temperature. Thus, physical and mechanical properties in the LOP at the backside are expected to vary with LOP thickness. The correlation between the measured conductivity and the LOP defect thickness through the LOP microstructure properties will thus be strongest when the fabrication procedure uses the same essential variables. The capability of the MWM sensor to detect and characterize LOP defects allows the MWM sensors to replace liquid penetrant inspections for this FSW.

As illustrated in FIG. 9, the MWM measured minimum conductivity near the center of the weld correlates with the LOP defect thickness when the MWM windings are oriented parallel to the weld axis. This minimum MWM response increases with increasing LOP defect thickness starting with the 0.02-in. LOP defect thickness level. It was not possible to distinguish between the zero defect and 0.02-in. LOP defect conditions using this response feature alone and a single-sense signal MWM. Even the use of two-dimensional images of the conductivity data, shown later in FIG. 12, did not provide sufficient information to distinguish between the 0.02-in and the zero defect conditions. A lower frequency, deeper penetration measurement with a larger MWM sensor spatial wavelength may provide the additional information required distinguishing between the zero defect and 0.02-in. defect conditions. Alternatively, higher frequency measurements that only respond to the near surface microstructural variations or multiple frequency measurements may provide information for discriminating between zero and shallow LOP defects.

Figure 10:
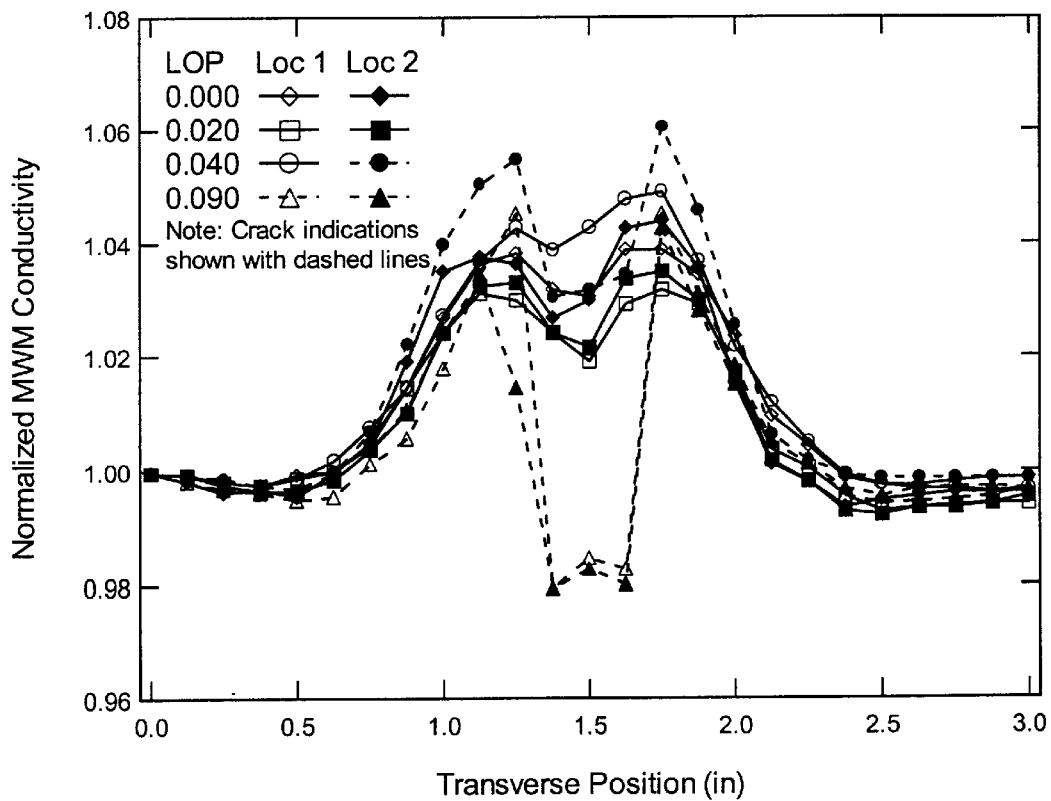
FIG. 10 is a plot of the normalized effective conductivity profile for similar metal FSW specimens with a single element MWM oriented perpendicular to the weld.
Figure 11:
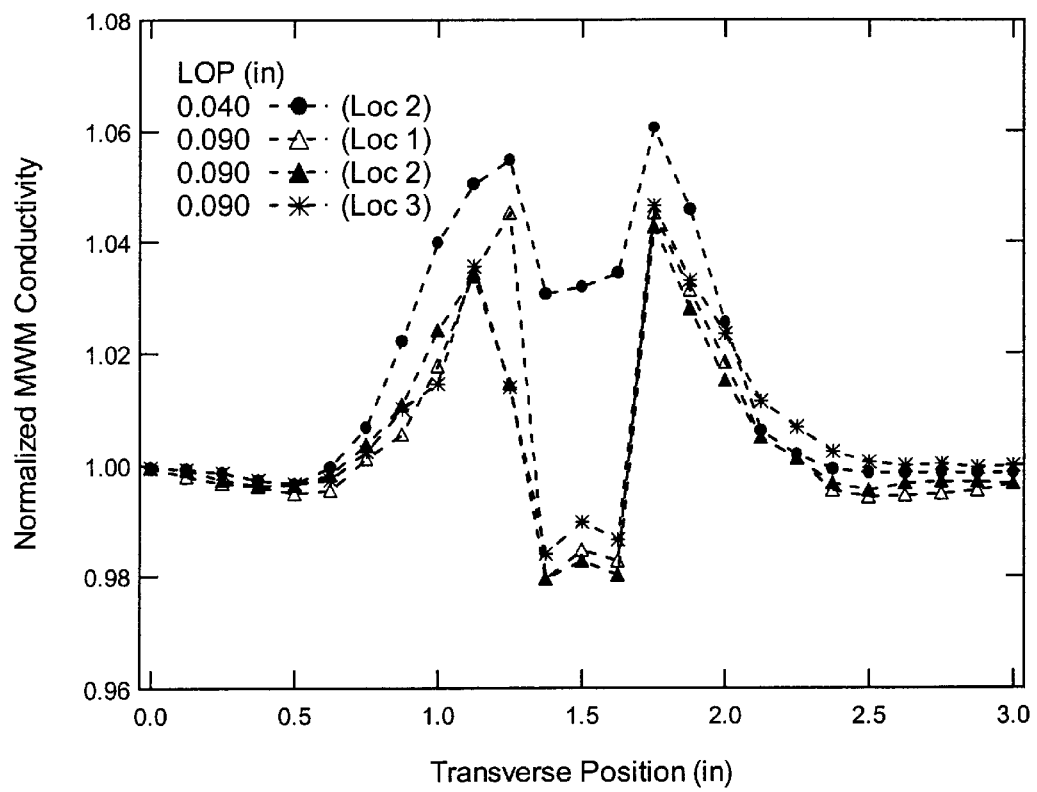
FIG. 11 is a plot of the normalized effective conductivity profile for similar metal FSW specimens showing crack indications with a single element MWM oriented perpendicular to the weld.

FIG. 10 shows plots of the normalized conductivity for transverse scans across the weld with the longer segments of the primary windings perpendicular to the weld. These scans correspond to Mode B of FIG. 6 and used the sensor illustrated in FIG. 2. The sensor was manually scanned across the weld in 0.25 inch (6.35 mm) increments. The drastic drop in MWM measured conductivity in the weld center region for both the 0.040-in. LOP and 0.090-in. LOP specimens is typical of MWM crack detection in the FSWs. The crack in the 0.040-in. LOP specimen appeared only over a portion of the specimen, while the crack in specimen 0.090-in. LOP specimen appeared to span the length of the specimen. A characteristic feature of a crack detection when the MWM is scanned, in Mode B of FIG. 6, across a crack is that the conductivity is abruptly reduced and remains reduced until the crack leaves the MWM footprint. As shown in FIG. 11, four different line scans had this characteristic. For these "crack" locations, the MWM measurements, with a parallel orientation of the longer winding segment, of FIG. 7 did not have a minimum in the weld center. Indeed, these scans show maximum conductivity near the center of each weld. This conductivity maximum near the weld center for the parallel orientation scans indicate that neither DXZ nor TMZ penetrated to the back side and may indicate a susceptibility to cracking.

Figure 12:
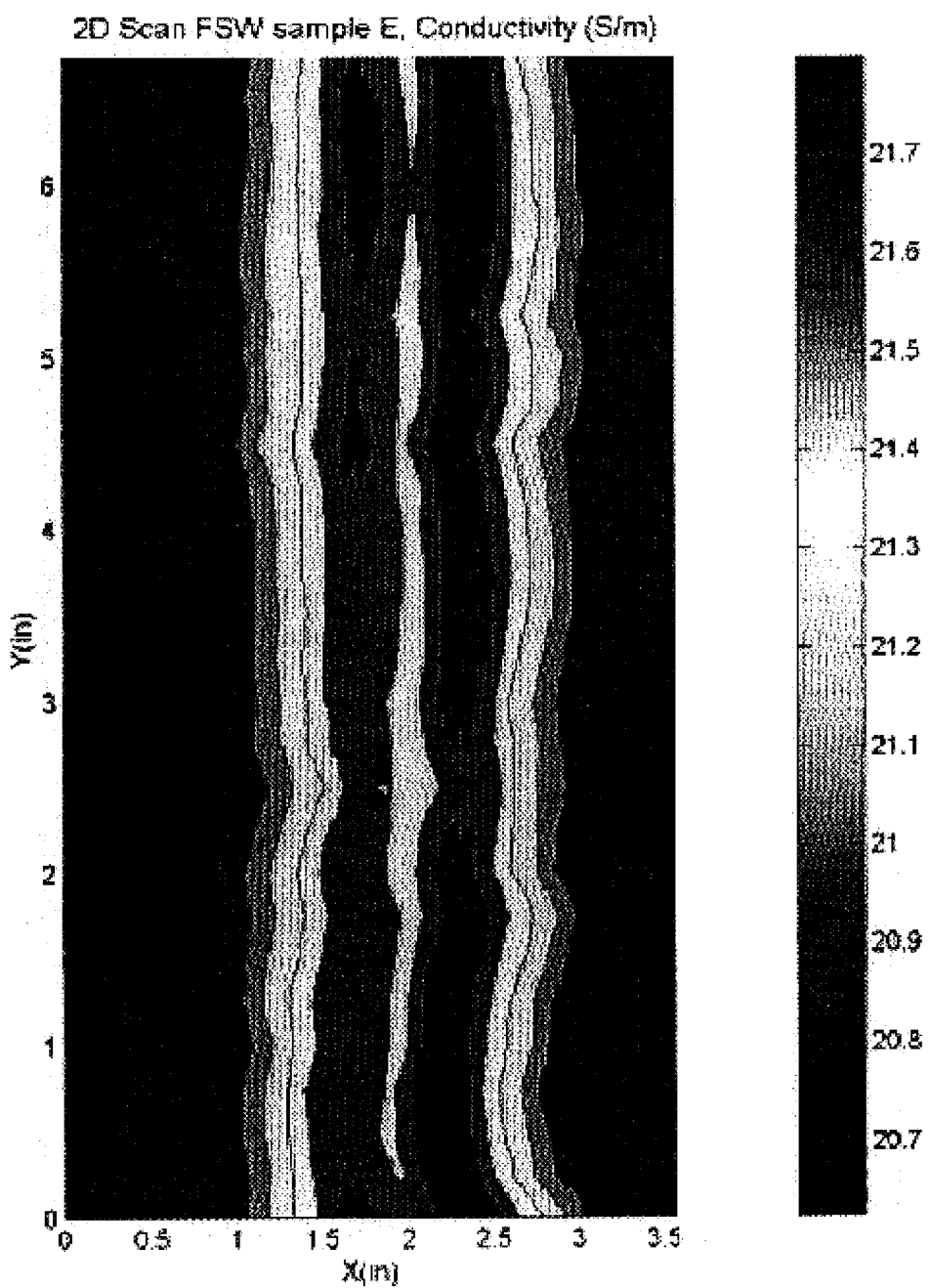
FIG. 12 is a two-dimensional image of the absolute MWM electrical conductivity of a similar metal FSW specimen obtained with continuous data acquisition for a single element MWM in a transverse scan and a linear encoder to determine the transverse position.
Figure 13:
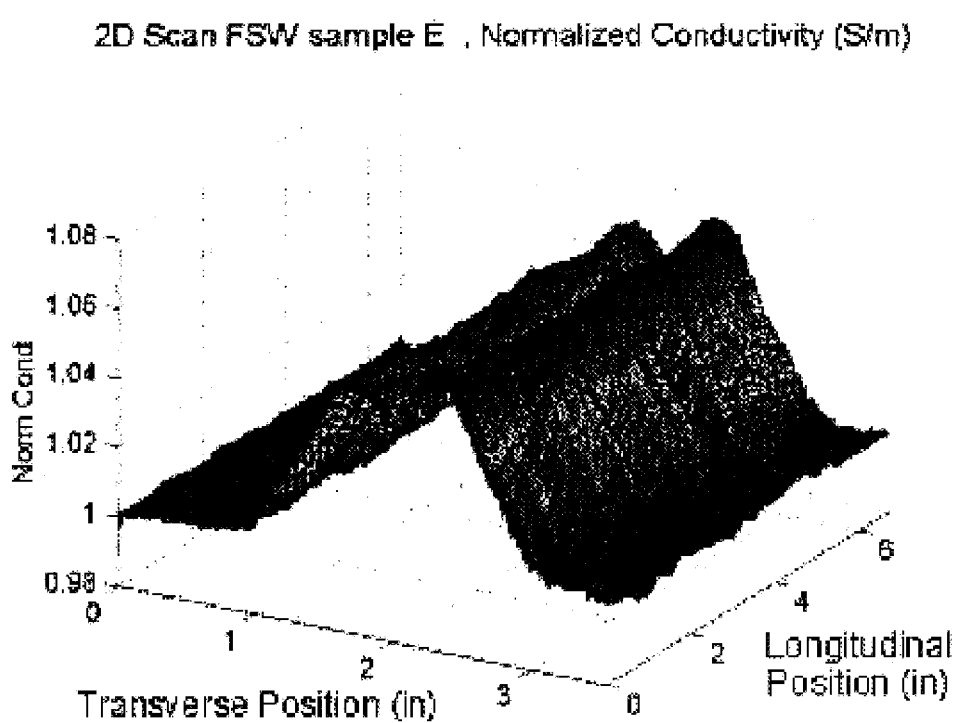
FIG. 13 is an isometric or surface plot of the normalized conductivity data from the image of FIG. 12.

FIG. 7 and FIG. 10 showed one-dimensional scans across the weld. An alternative presentation for the data that more readily permits visual inspection of the entire length of the weld is to display the property data as two-dimensional images. While these images can be created by manually moving the sensor across and along the weld, the use of automated scanners and position encoders to provide continuous position information can greatly enhance the quality of the images. FIG. 12 shows a two-dimensional image of the absolute electrical conductivity obtained with continuous data acquisition in a series of transverse scans with a linear encoder to determine the transverse position. A transverse scan was taken every 0.25 inches (6.35 mm) along the length of the FSW, which had a 0.02-in. LOP defect. In these measurements the longer segments of the primary winding were oriented parallel to the weld. FIG. 13 shows the same data as a normalized conductivity, consistent with FIG. 8, in an isometric surface plot format. This surface plot shows both the consistency of the weld quality down the length of the weld and the local minimum in the normalized conductivity at the center of the weld used for LOP defect sizing. FIG. 8 can be considered an "end-view" of the surface plot.

In another embodiment, sensing arrays comprising at least one drive winding and multiple sensing elements are used to inspect the FSW. An example array is shown in FIG. 5. The sensing elements have dimensions small enough to provide an imaging resolution suitable for measuring the width of the weld zones at or near the surface, e.g., HAZ at the crown of a fusion weld, HAZ and weld metal at the root of a fusion weld, or DXZ, TMZ, and HAZ regions at the back surface of an FSW. The sensing elements are aligned into a linear array so that two-dimensional images of the material properties in the weld region can be created when the array is scanned across or along the weld.

The capability of high-resolution arrays to provide detection and sizing of LOP defects was demonstrated on FSW samples for both similar metal welds and dissimilar metal welds. This group of samples used a different fabrication procedure than the first group, described above. For the similar metal welds, two plates of Al 2195 were joined. For the dissimilar metal welds, an Al 2219 plate was joined to an Al 2195 plate. Each FSW specimen was examined in a continuous scanning mode with the array of FIG. 5. A single scan used 15 or 16 elements in each row of sensing elements and spanned a distance of about 1.1 inches (27.9 mm) perpendicular to the scan direction. The length of scans along the samples (Mode D of FIG. 6) was between 3 inches (76 mm) and 10 inches (254 mm) and transverse to the weld (Mode B of FIG. 6) was approximately 2 inches (50.8 mm). Transverse scan speeds were 0.05 inch/sec (1.1 mm/sec). Longitudinal scan speeds ranged from 0.13 inch/sec (3.3 mm/sec) to 1.6 inch/sec (40.6 mm/sec); the higher scan speeds did not substantially degrade the quality of the measurement. The data was acquired in a fully parallel manner using multiple channel impedance measurement instrumentation, as disclosed in U.S. Provisional Application No. 60/248,104, the entire teachings of which are incorporated herein by reference. The scans were performed with a one-dimensional automated scanner. In these measurements, the excitation frequency ranged from relatively low, at 251 kHz for modest penetration of the magnetic field into the MUT, to relatively high at 3.98 MHz, to determine the near-surface effective electrical conductivity and proximity of the sensor to the MUT.

Figure 14:
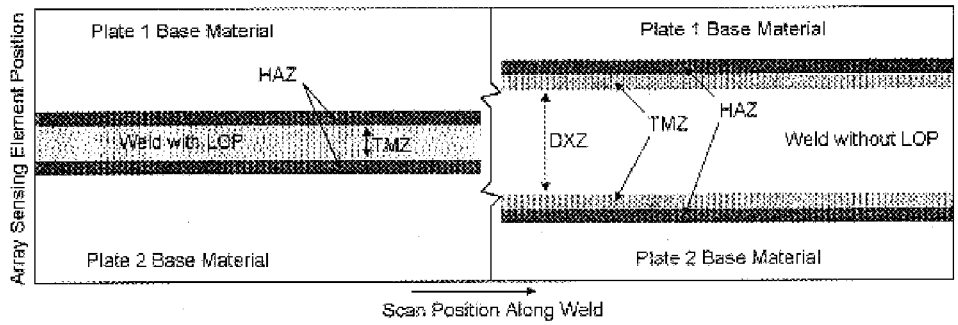
FIG. 14 is a schematic of a two-dimensional image of the backside effective electrical conductivity of a similar metal FSW specimen obtained with a longitudinal scan of high-resolution MWM-Array with longer segments of the primary winding oriented perpendicular to the weld axis, the specimen having an LOP defect on the left side but having no LOP defect on the right.
Figure 15:
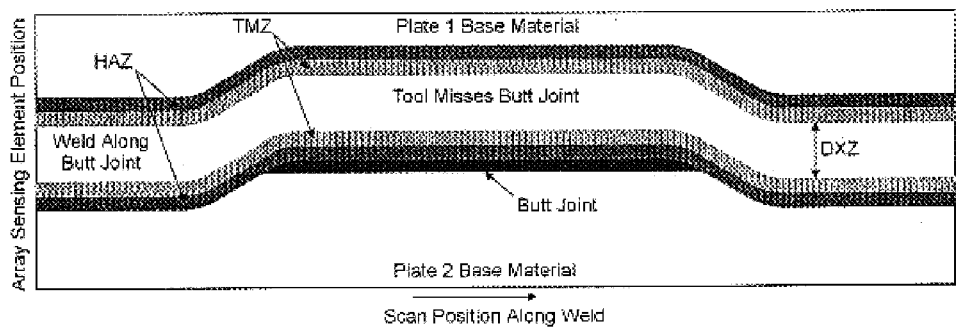
FIG. 15 is a schematic of a two-dimensional image of the backside effective electrical conductivity of a similar metal FSW specimen obtained with a longitudinal scan of high-resolution MWM-Array with longer segments of the primary winding oriented perpendicular to the weld axis, the specimen having the weld alignment varied with respect to the butt joint between the plates.
Figure 16:
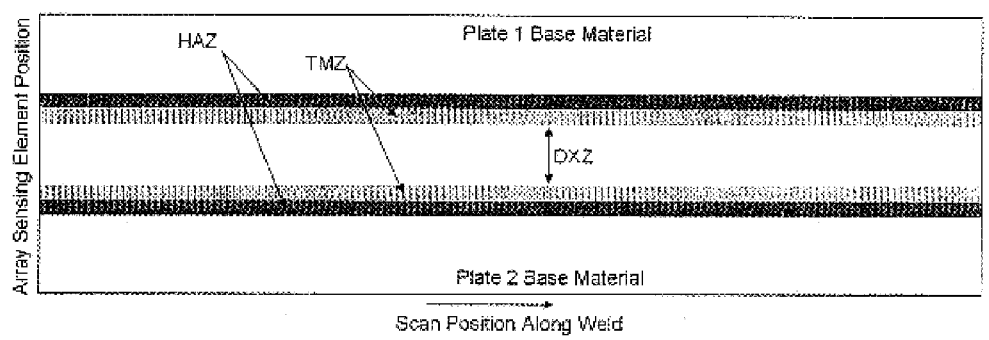
FIG. 16 is a schematic of a two-dimensional image of the backside effective electrical conductivity of a zero LOP defect specimen obtained with a longitudinal scan of high-resolution MWM-Array with longer segments of the primary winding oriented perpendicular to the weld axis.

One method for inspecting the welds for defects involves making longitudinal scans with the longer segments of the primary winding oriented perpendicular to the weld (Mode D of FIG. 6). This imaging capability is illustrated in FIG. 14 for a scan down the back side of a FSW between two aluminum alloy plates. For this weld, the tool tip plunge depth was varied. On the left, the weld had an LOP defect such that the DXZ (nugget) was separated from the back side surface by TMZ. On the right the plunge depth was sufficient so that no LOP defect was present and there was a wide DXZ in the center flanked by nonrecrystallized TMZ and HAZ outside the TMZ. Another example image is shown in FIG. 15 for a scan down a weld with variable alignment of the FSW tool with respect to the butt joint between the aluminum alloy plates. In the middle area of FIG. 15 the joint between the materials is visible on the back side, indicating that the tool was not aligned with the joint. This FSW can have no LOP and yet would not be considered adequate. MWM-Array scans would readily detect this unacceptable condition (a "planar flaw"). When the weld region is wider than the sensing array, multiple scans of the array can be used to capture as much of the weld zone property variations as possible in the image. In each image, variations of the normalized conductivity accurately reflect microstructural variations. The detailed and quantitative local variations in the microstructural properties obtained in these scans indicate the potential to replace etching and penetrant testing as a weld inspection method. The imaging capability is illustrated further in property maps as shown in FIG. 16 for a zero LOP defect weld and FIG. 17 for a 0.06-in. LOP defect, and intermittent planar flaws.

Figure 17:
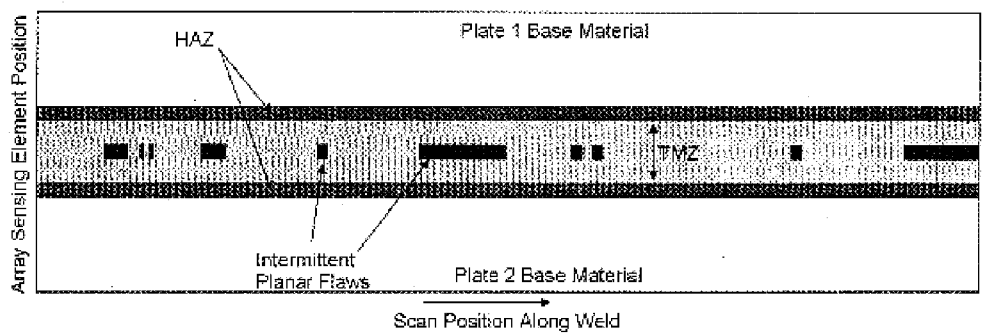
FIG. 17 is a schematic of a two-dimensional image of the backside effective electrical conductivity for an LOP defect specimen obtained with a longitudinal scan of high-resolution MWM-Array with longer segments of the primary winding oriented perpendicular to the weld axis, the specimen also having intermittent planar flaws.

The presence of intermittent flaws is readily detected by a precipitous drop of conductivity. Often, these intermittent flaws are aligned along the original butt joint. FIG. 17 shows a schematic for a conductivity image for a 0.06-in. LOP defect in a FSW that also contains intermittent planar flaws or cracks. Here again DXZ is separated from the back side surface by TMZ. In the FSWs illustrated on the left side of FIG. 14 and in FIG. 17, an image obtained at high frequencies would reveal TMZ and HAZ, whereas a sufficiently low frequency image could bring out the DXZ as well. This is contrasted with the image of a zero LOP defect specimen (FIG. 16) that shows high frequency conductivity image along the FSW indicative of a wide uniform DXZ. This demonstrates a rapid inspection capability for the weld, as the array captures the entire conductivity profile when the sensor is scanned down the welds. In addition, the high-resolution image captures the essential features of the weld and can replace etching, which only provides a visual, non-quantitative, measure of the quality of the weld and is not environmentally friendly.

Another method for inspecting the welds for defects involved making transverse scans with the longer segments of the primary winding oriented parallel to the weld (Mode B of FIG. 6). For these transverse scans, connection to a one-dimensional automated scanner allowed high resolution (up to several thousand data points) to be obtained when traversing the weld. The individual channels from the MWM-Array allowed independent measurements of different sections along the length of the weld that permitted images of the scanned area properties to be created with a single pass of the sensor array.

Figure 18:
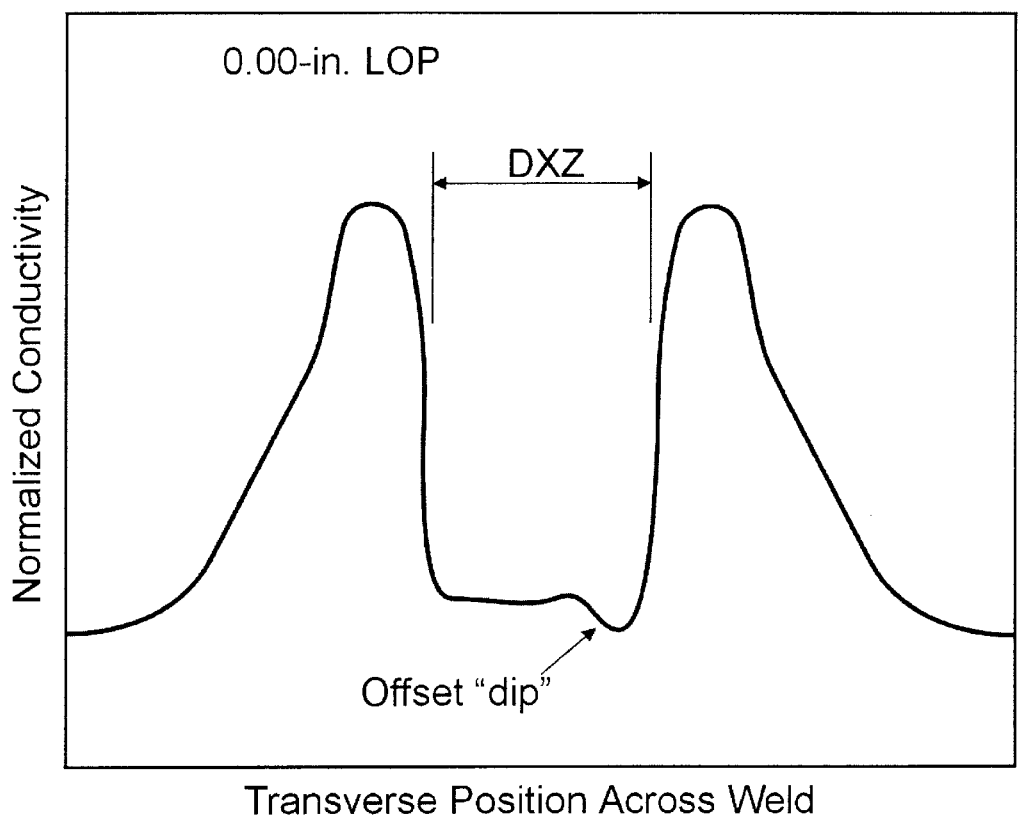
FIG. 18 is a schematic of the normalized conductivity for a measurement channel of a high-resolution MWM-Array with longer segments of the primary winding oriented parallel to the weld axis for a similar metal zero LOP defect specimen.
Figure 19:
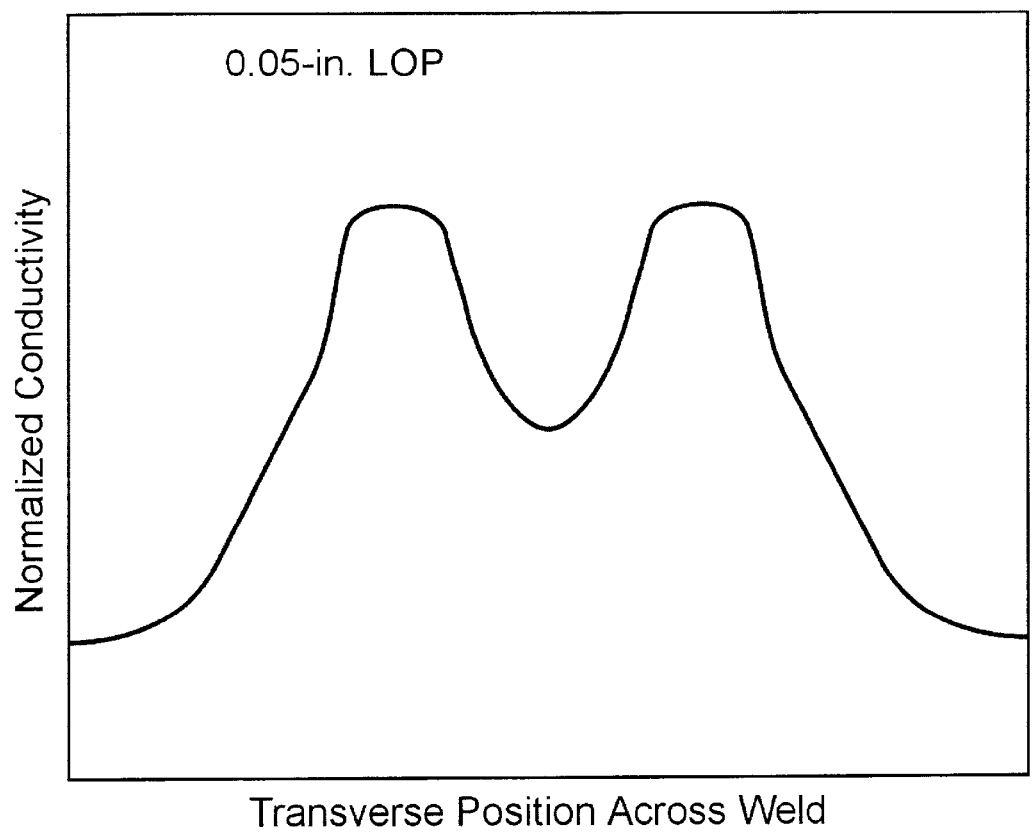
FIG. 19 is a schematic of the normalized conductivity for a measurement channel of a high-resolution MWM-Array with longer segments of the primary winding oriented parallel to the weld axis for a similar metal 0.05-in. LOP defect specimen.

A schematic cross-sectional plot of the measured conductivities across the weld is shown in FIG. 18 for a zero LOP defect specimen and in FIG. 19 for a 0.05-in LOP defect specimen. A relatively low conductivity in the central region reflects a measurement of the DXZ. The surrounding higher conductivity regions reflect the properties of the HAZ and TMZ. The outermost regions reflect the properties of the base materials of the plates being joined. The shape of this conductivity profile for an FSW is similar to the conductivity profile obtained with conventional eddy current sensors on fusion welds (Nondestructive Testing Handbook, 1986), except an MWM-Array permits obtaining the entire profile across the weld simultaneously by the array of sensing elements when the array is sufficiently wide. In addition, the data can be obtained with only an air calibration of the sensor, as opposed to the use of conventional eddy current sensor measurements that require calibration on reference standards of known conductivity. With an air calibration approach, calibration of the sensor is performed by measuring the response in air and grid measurement methods are used to determine the absolute electrical conductivity. See U.S. Pat. No. 6,188,218, the entire teachings of which are incorporated herein by reference.

Figure 20:
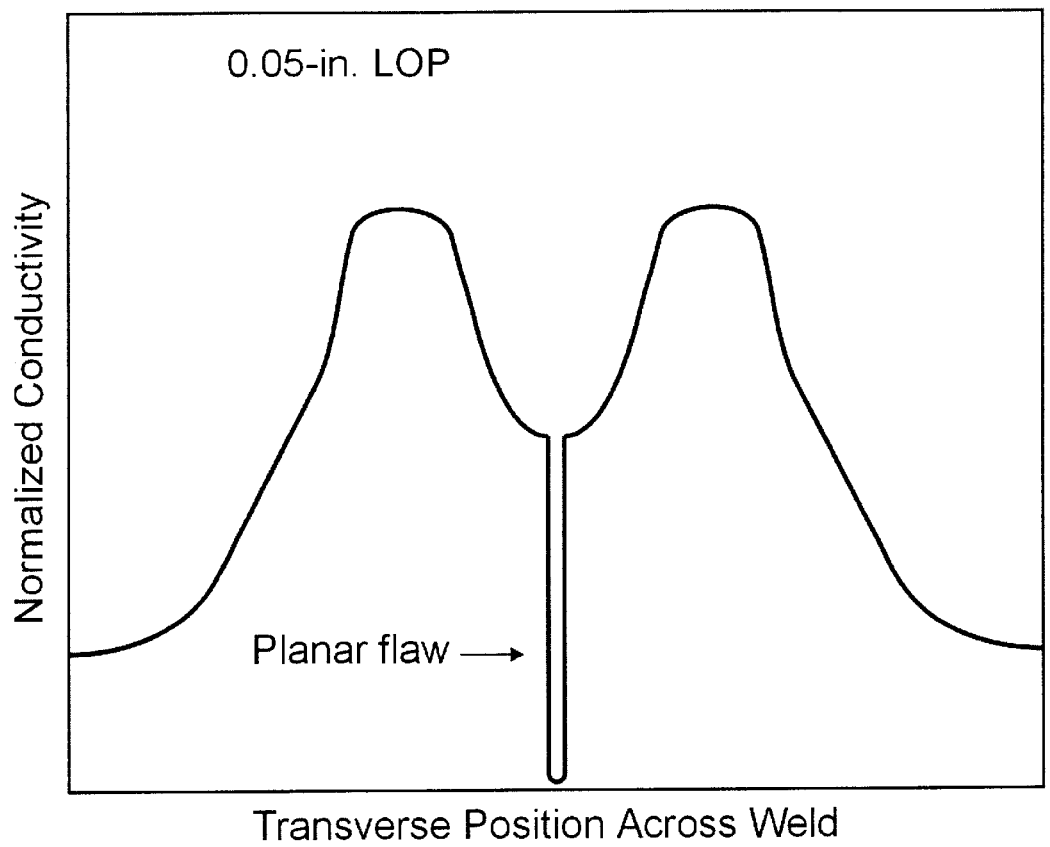
FIG. 20 is a schematic of the normalized conductivity for a measurement channel of a high-resolution MWM-Array with longer segments of the primary winding oriented parallel to the weld axis for a similar metal 0.04-in. LOP defect specimen which also has intermittent planar flaws.

For the scans illustrated in FIG. 18 and FIG. 19, the conductivity was normalized by taking the ratio of the measured conductivity to the average conductivity measured for the base metal. High-resolution scans provide several features that permit the discrimination of no-LOP defect FSWs from FSWs with an LOP. One such feature is a wide, relatively low conductivity zone with an "offset minimum," i.e., with a local conductivity dip at an edge of the DXZ as illustrated in FIG. 18. This local offset minimum only appears in the no-LOP plates and provides an easily observed visual representation. As illustrated in FIG. 19 and FIG. 20, this feature did not exist in the welds with LOP defects. The conductivity profiles for FSWs with LOP have a distinctly different center zone shapes and widths compared to FSWs with no LOP, as illustrated in FIG. 18 and FIG. 19. FIG. 20 shows a conductivity profile for a FSW with LOP and a planar flaw. The latter is reflected in a precipitous drop in the electrical conductivity.

Quantitative features from the conductivity data obtained with high-resolution scans facilitate weld quality assessment and permit automation of accept/evaluate decisions required for production applications. In production environments, these features can be obtained with longitudinal scans using a high resolution MWM-Array and should be sufficient to qualify most good welds and identify a suspect population. Transverse scanning with its inherently higher resolution may be required locally for evaluation of suspect sections identified by longitudinal scans. This evaluation should provide discrimination between relatively small LOP defects that might not be detrimental, e.g., less than 0.05 in., and larger LOP defects and, thus, provide a basis for acceptance or rejection.

Figure 21:
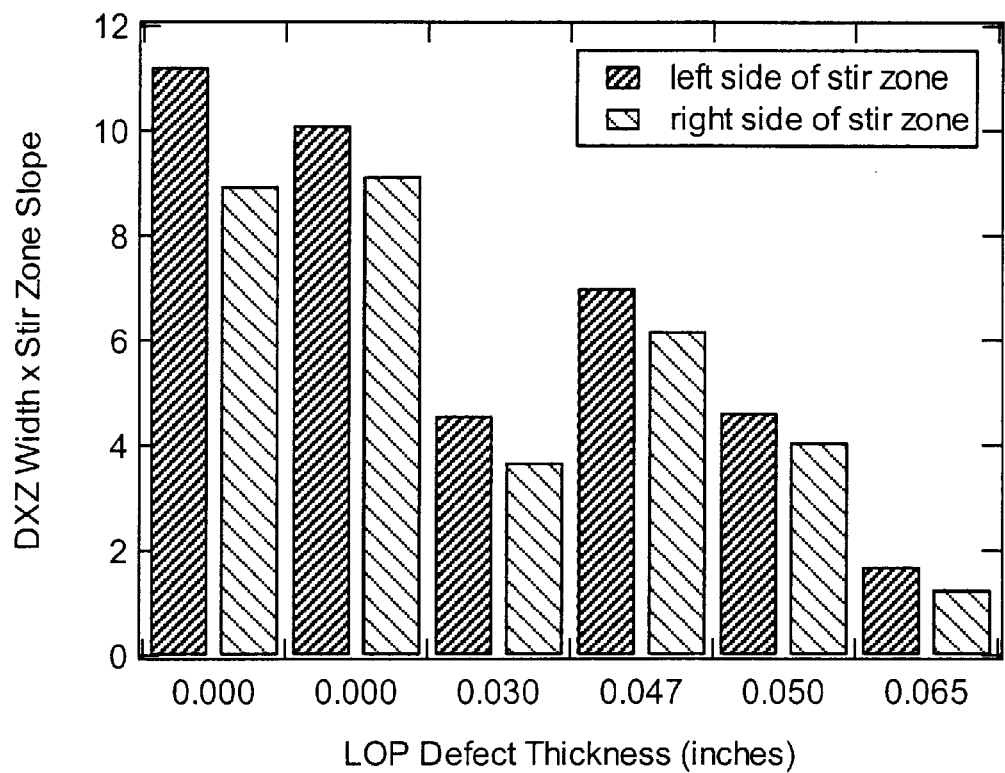
FIG. 21 is a plot of the DXZ width times stir zone slope feature versus the LOP defect thickness for similar metal FSW.

One simple quantitative feature is the product of the width of the center zone multiplied by the slope of the sides of this zone. The slope at the sides and the width are computed from a derivative image, which requires many data points in this region. This product is plotted as a function of LOP defect size in FIG. 21. Another simple feature is the measurement of the width of the DXZ or the center zone of the conductivity profile. This permits the assignment of welds into three categories: (1) good for welds with a relatively wide center zone, (2) bad for welds with a relatively narrow center zone, and (3) suspect for welds with intermediate center zone widths. If scans on additional panels confirm that no-LOP FSWs have wide center zone widths that are distinctly greater than in the FSWs with LOP less than 0.050-in., then this simple feature would be sufficient and may be robust enough alone to qualify good welds. If significant portions of good welds fall in the intermediate range, or if some good welds have the width-slope product comparable to the 0.047-in. LOP defect shown in FIG. 21, then one of the additional features, such as the presence of the local conductivity dip at an edge of the DXZ observed on the no-LOP specimens or other shape filters, would be required to further evaluate these welds. Another feature that can reflect the quality of the weld is the value of the minimum of the electrical conductivity in the center region of the weld, which tends to be relatively for no-LOP FSW. The use of a shape matching filter could provide a robust characterization of the weld quality since it uses all of the information in the conductivity profile. An example shape matching filter could compare the measured conductivity profile to the profile of a reference FSW known to be without defects. No-LOP defect welds would have a high correlation with the reference FSW while FSWs with LOP would have a low correlation. Moreover, differences between FSWs with different LOP thickness can be readily recognized and even quantified by a variety of image recognition techniques. These techniques can be applied to 2-D or 3-D images of conductivity, including conductivity of the nugget itself.

One protocol for FSW inspection is to scan with a longitudinal high resolution MWM-Array at a high frequency, such as 4 MHz, and to categorize welds into wide, intermediate and narrow. Then for suspect sections of the FSWs, local transverse scans should be performed at several locations to identify the local off-center minimum feature typical of good welds and employ other shape filters. If this feature is not present and/or the weld does not pass appropriate shape filters, the weld would be categorized as having a LOP defect.

Figure 22:
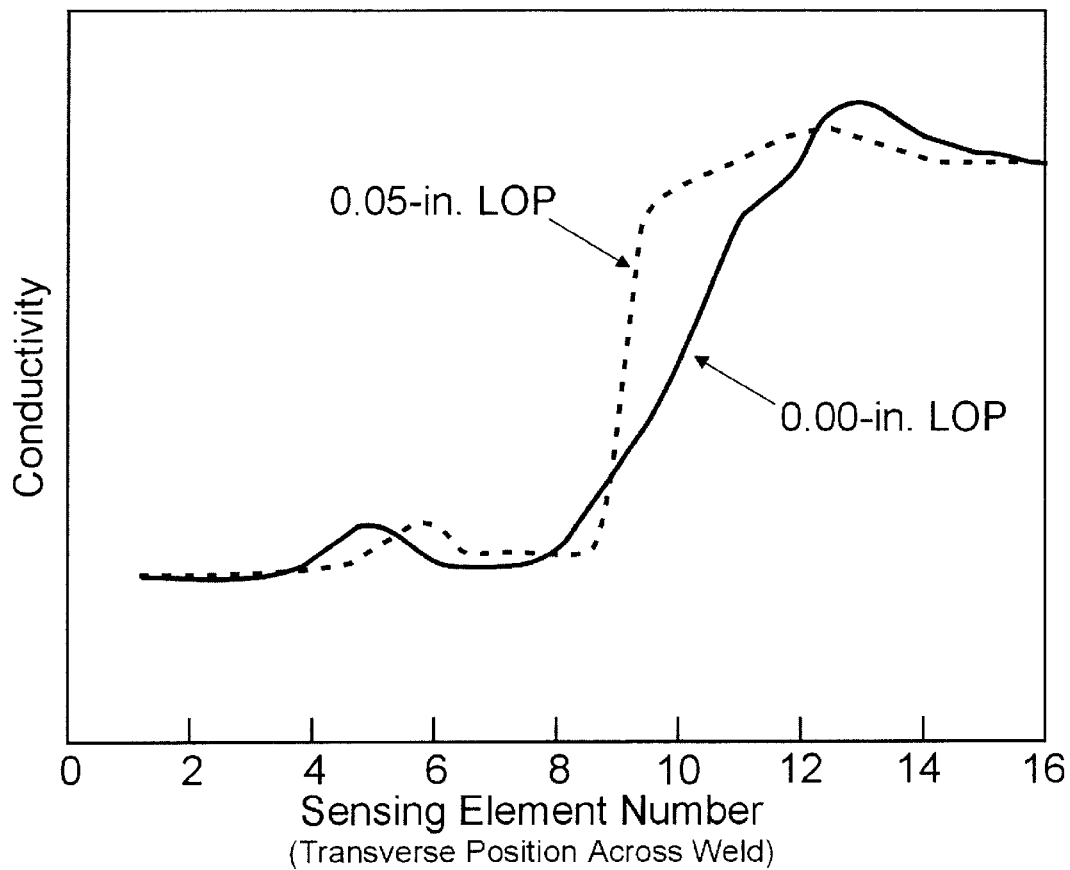
FIG. 22 is a schematic of the effective electrical conductivity profile for dissimilar metal FSWs for zero and 0.05-in. LOP defect specimens obtained with transverse scans of high-resolution MWM-Arrays with longer segments of the primary winding oriented parallel to the weld axis.
Figure 23:
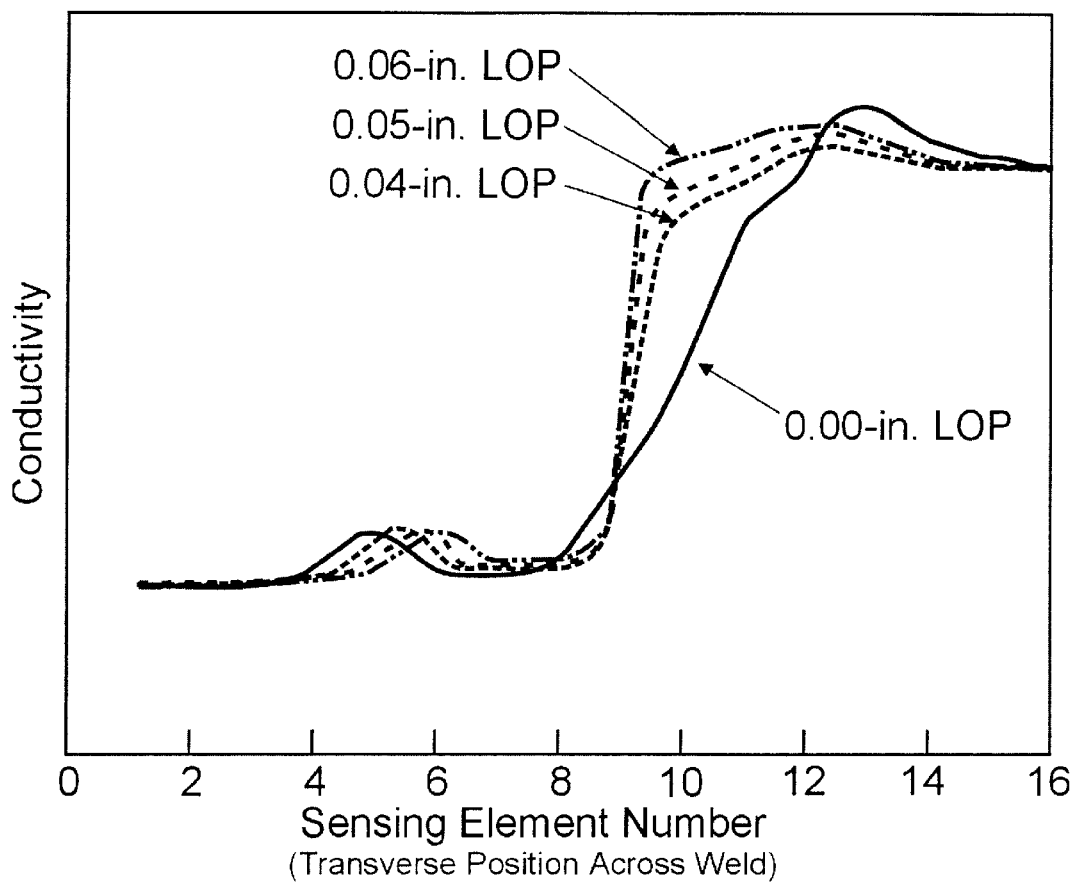
FIG. 23 is a schematic of the average conductivity profile across several dissimilar metal FSWs obtained with a high-resolution MWM-Array.

Longitudinal scans along FSWs with the longer segments of the primary winding of an MWM-Array oriented perpendicular to the weld (Mode D of FIG. 6) can also be used to determine the quality of the welds between dissimilar metals. A representative plot of the effective conductivity profile across the weld (as indicated by the sensor element channel number) is shown in FIG. 22 for a no-LOP defect weld and a 0.05-in. LOP defect weld. In this case, relatively small variations in the conductivity across the weld are masked by the large differences in the electrical conductivity of the base materials. One distinguishing feature of the weld quality is the sharpness of the transition of the electrical conductivity between the two metals. As indicated in FIG. 23, welds with an LOP defect have a sharp transition in the electrical conductivity while welds without an LOP defect have a more gradual transition. This appears to reflect the quality of the mixing of the base materials by the FSW process, with defective welds not being mixed well enough. A metric for determining the weld quality is found by normalizing the measured conductivity at sensing element 10, which provides a measure of the weld condition and one plate base material conductivity, by the measured conductivity at sensing element 1, which reflects the base material conductivity for the other plate. A normalization routine accounting for conductivity of both base metals can also be used. More sophisticated filters based on the shape of the entire conductivity profile of FIG. 23 can also be used. Images of the conductivity down the length of the weld, similar to FIG. 16, can also be created for visual inspection of the weld quality.

In one embodiment, a single high frequency measurement is made of conductivity and proximity at each sensing element to measure only the near surface properties of the material in the weld. In another embodiment, multiple frequencies are used to determine the variation of material properties with depth from the surface. This includes the generation of three dimensional images of the DXZ using model based methods that model the magnetic field interactions with the nugget using either analytical methods or numerical methods (e.g., finite element methods). In one embodiment, the model is used to generate measurement grids and higher dimensional databases, respectively, of sensor responses to the DXZ zone property variations. Example estimated properties of the DXZ are the width of the penetration region at the base of the weld and the width of the DXZ at a selected depth from the base of the weld. The multiple frequency imaging method is then used to estimate these two parameters using a combination of measurement grid table look-ups, and intelligent root searching methods.

Determining the thickness and microstructural variations within the near-surface LOP zone are an extension of the multiple frequency coating characterization and property profiling methods described in U.S. patent application Ser. 09/191,668, the entire contents of which are incorporated herein by reference. The multiple frequency coating characterization algorithm can be used to independently estimate three unknown material properties simultaneously (Goldfine, 2001). For the LOP zone in a friction stir weld, this algorithm can be used to estimate the absolute conductivity in the LOP zone and its thickness independently. Combined with the use of high-resolution MWM-Array sensing elements, this permits three-dimensional imaging of the LOP zone. The sensor array can also be used to characterize subsurface features such as porosity, cracks, lack of fusion, material condition and properties before and after heat treatment (or other processes), as well as other material anomalies or property distributions that affect metal product, component, or weld quality.

Figure 24:
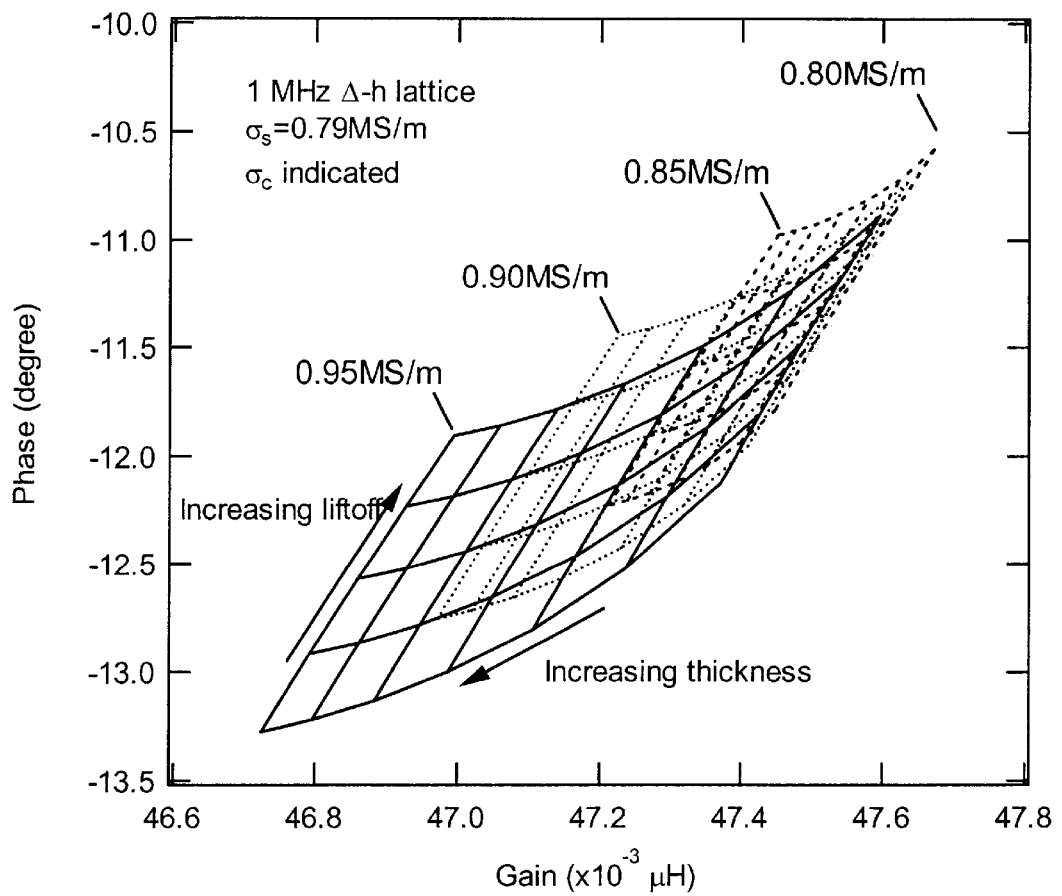
FIG. 24 shows a representative coating thickness/lift-off grid lattice for turbine blade materials.

In the coating characterization algorithm, sensor responses for ranges of property variations are calculated and stored in databases. In this algorithm, the measurement grids provide a two-dimensional database of the sensor response. The grids are created in advance by varying the coating thickness (or LOP zone thickness), and lift-off over the range of interest for a given coating conductivity (or LOP zone conductivity). In a grid lattice, measurement grids are created for a range of coating conductivities that span the range of interest for a given material, forming a three-dimensional database for the sensor response. A representative grid lattice for the characterization of turbine blade coatings is shown in FIG. 24. The lattice shows coating thickness-lift-off grids for four coating conductivities at a single frequency. In each measurement grid, the spacing between the grid points illustrates the sensitivity for independently estimating the coating thickness and the lift-off. The grid spacing and sensitivity is large when the coating and the substrate have significantly different conductivities; the grid collapses when the conductivities of the coating and the substrate are equal, which is expected for an uncoated specimen.

The coating characterization algorithm uses the measurement grid lattices to determine a set of coating properties (such as LOP conductivity, LOP thickness, and lift-off) that are independent of frequency. Alternatively, a non-linear least squares method can be used to minimize the error between the predicted response from a model for the property variations with depth and the measured data at multiple frequencies and/or multiple lift-offs. Computationally, the grid lattice approach, which only uses table look-ups and simple interpolations, tends to be faster than the non-linear least squares approach, which generally require multiple calculations from simulation model that can be complicated. Hybrid methods can improve the speed of the non-linear least squares approach and permit a real-time measurement capability by using precomputed grid lattices for the sensor responses in place of the calculations from the model.

Figure 25:
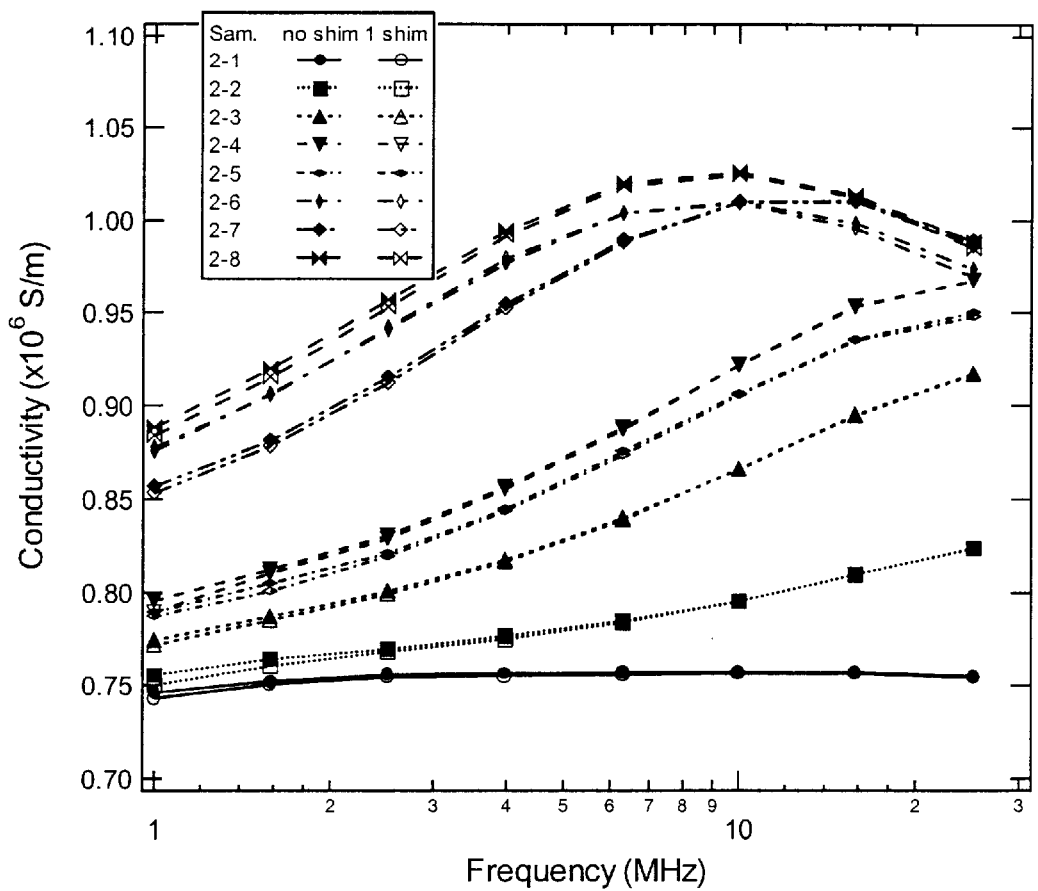
FIG. 25 is a plot of the multiple frequency conductivity measurements for MCrAlY coatings on IN738 substrates obtained with a single element MWM.
Figure 26:
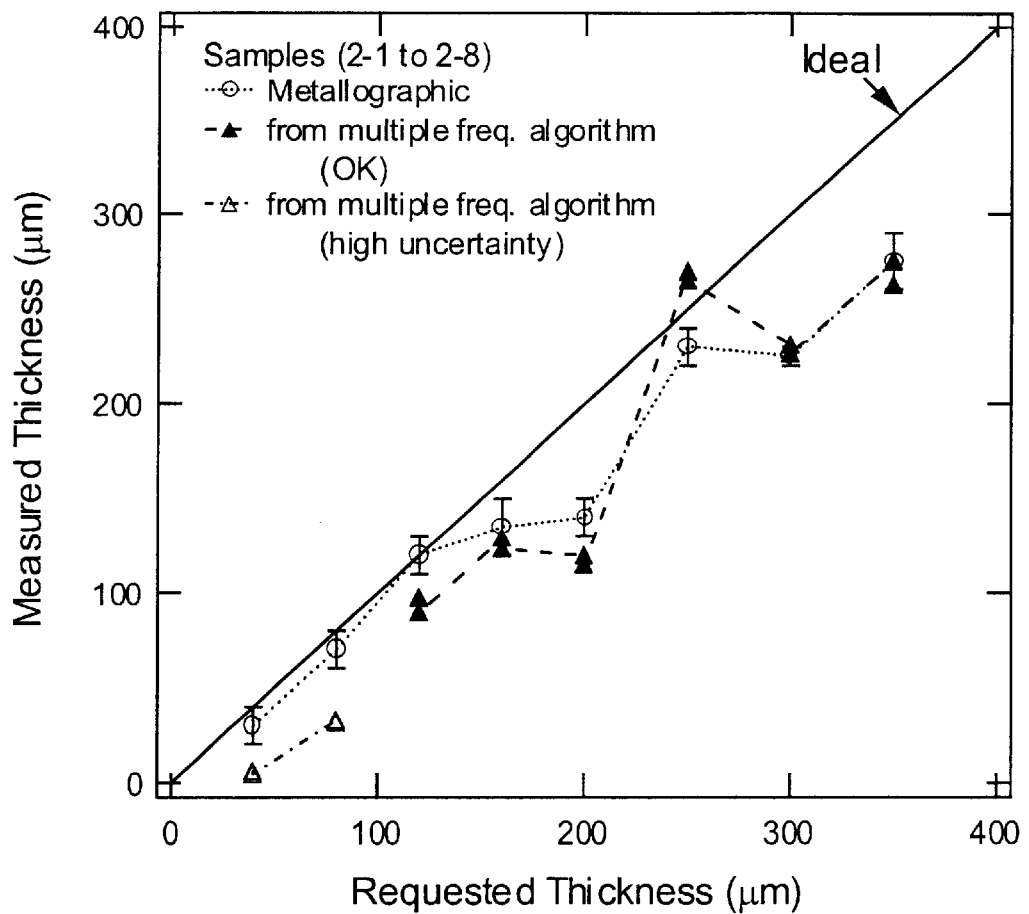
FIG. 26 shows a comparison between the coating thickness determined from the coating characterization algorithm, using the data of FIG. 25, and metallography.

A representative application of the three-parameter estimation algorithm is the determination of coating conductivity, coating thickness, and lift-off of a MCrAlY bond coat on an IN738 substrate. The effective conductivity is plotted against the frequency in FIG. 25. For the uncoated specimens, the conductivity is constant with frequency. For the coated specimens, the low-frequency response approaches the substrate conductivity as the skin depth of the magnetic field becomes large compared to the coating thickness. The high-frequency response approaches the coating conductivity as the skin depth of the magnetic field becomes small compared to the coating thickness. The data with a 25 micron (1 mil) thick shim placed between the sensor and the specimens yields exactly the same effective conductivity estimate as the data without a shim, which provides confidence in the quality of the calibration and the measurements. As shown in FIG. 26, there is good agreement with destructive metallographic measurements of the coating thickness for coatings thicknesses of 100 to 350 micrometers (0.004 to 0.014 in.)

One of the limitations of the use of inductive secondary coils in magnetometers is the depth of sensitivity to deep features, such as imaging of the nugget properties in an FSW. For a spatially periodic primary winding structure, the dimension of the spatial periodicity can be termed the spatial wavelength $\lambda$. The depth of penetration of the magnetic field into the MUT is then related to both $\lambda$ and the conventional skin depth; the penetration depth is limited to approximately $\lambda/6$ at low frequencies, and the skin depth at high frequencies. Thus, at low frequencies, increasing the wavelength increases the depth of penetration and allows the sensor to be sensitive to deeper features. However, the induced voltage on the secondary coils is proportional to the rate of change of the magnetic flux with time, or the excitation frequency, so that the frequency cannot be lowered indefinitely otherwise the signal is lost in measurement noise. To overcome these low-frequency limitations, alternative sensing elements based on solid-state device technology, such as Giant magnetoresistive (GMR) devices, Hall effect devices, and SQUIDS, can be used. In particular, sensing element arrays that use GMR sensors permit inspection measurements down to low frequencies, such as 50 Hz or even dc, for characterization of relatively thick plates, such as 0.5 inch aluminum-lithium alloy plates. The use of a GMR sensor as the sensing element in a magnetometer is described in more detail in U.S. Provisional Application No. 60/284,972, submitted Apr. 21, 2001, the entire teachings of which are incorporated herein by reference.

For magnetizable metal products, components, and welds, such as carbon steels and high-strength low-alloy steels, the GMR sensing element arrays can be used to map residual stress patterns and the geometry and properties of the HAZ and weld nugget. The measurements can be performed from DC to a high frequency. In one embodiment, scans are made with both GMR and inductive sensing elements from DC up to a high frequency, such as 10 MHz. The high resolution imaging with conformable eddy current sensor arrays that use a single wavelength drive winding with an array of sensing elements is a direct replacement for magnetic particle inspection and does not require paint removal. Furthermore, multiple frequencies can be used to measure the depth of cracks that are either surface breaking of subsurface.

Another technique for increasing the depth of penetration of an MWM-Array is to shape the magnetic field with the geometry of the primary winding. This allows for relatively long wavelength excitations with modest sensor footprints. An example is the circular sensor of FIG. 27, which has several circular drive windings 70 that are wound with differing numbers of turns. Connections 72 are made to each drive winding and the current flow direction in the windings is set to shape the magnetic field created by the drive windings. A sensing element, such as a magnetoresistive sensor (MR) 74 and/or inductive coil is placed at the center of the drive windings. Arrays of sensing elements and rectangular winding structures can also be used, as described in U.S. Provisional Application No. 60/284,972, submitted Apr. 21, 2001, the entire teachings of which are incorporated herein by reference.

Figure 27:
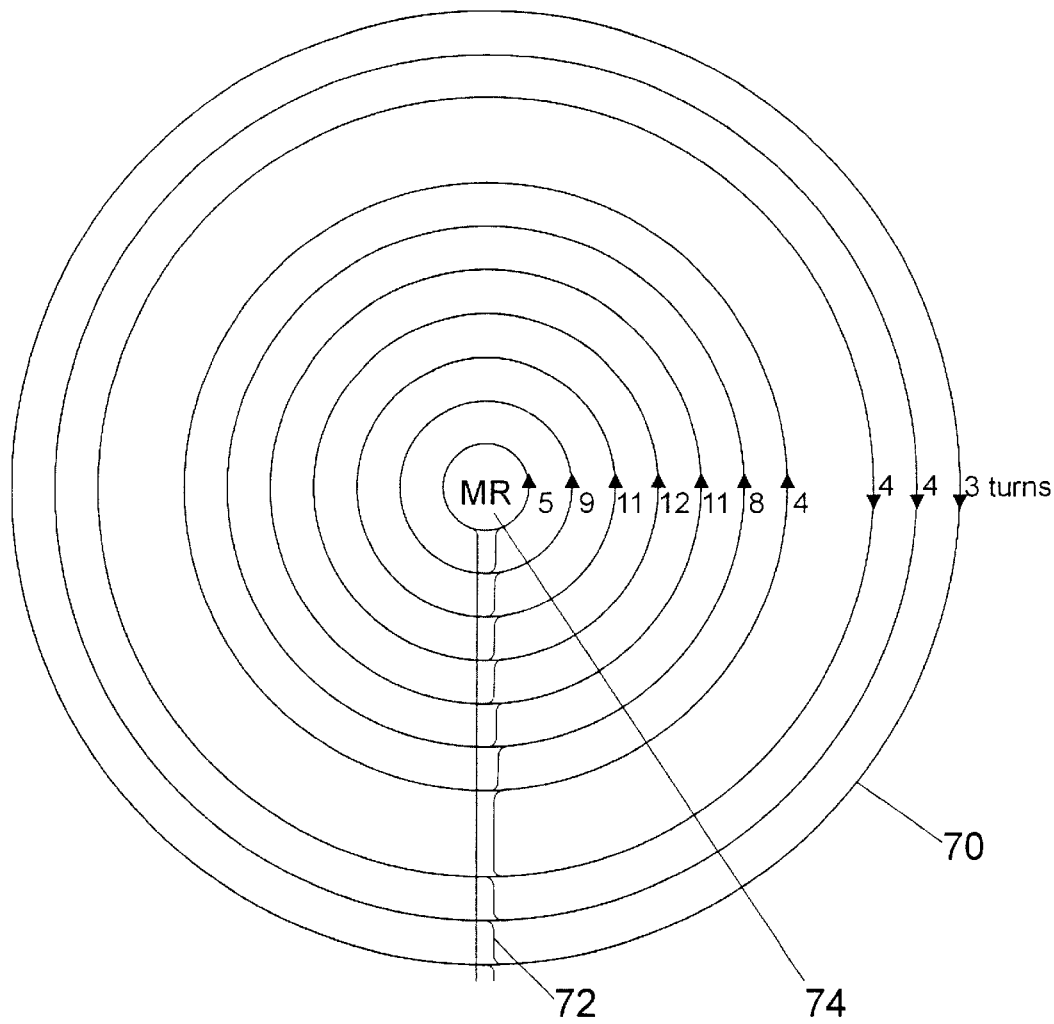
FIG. 27 shows a plan view of a circular shaped-field magnetometer containing a GMR sensor at the center of the structure.
Figure 28:
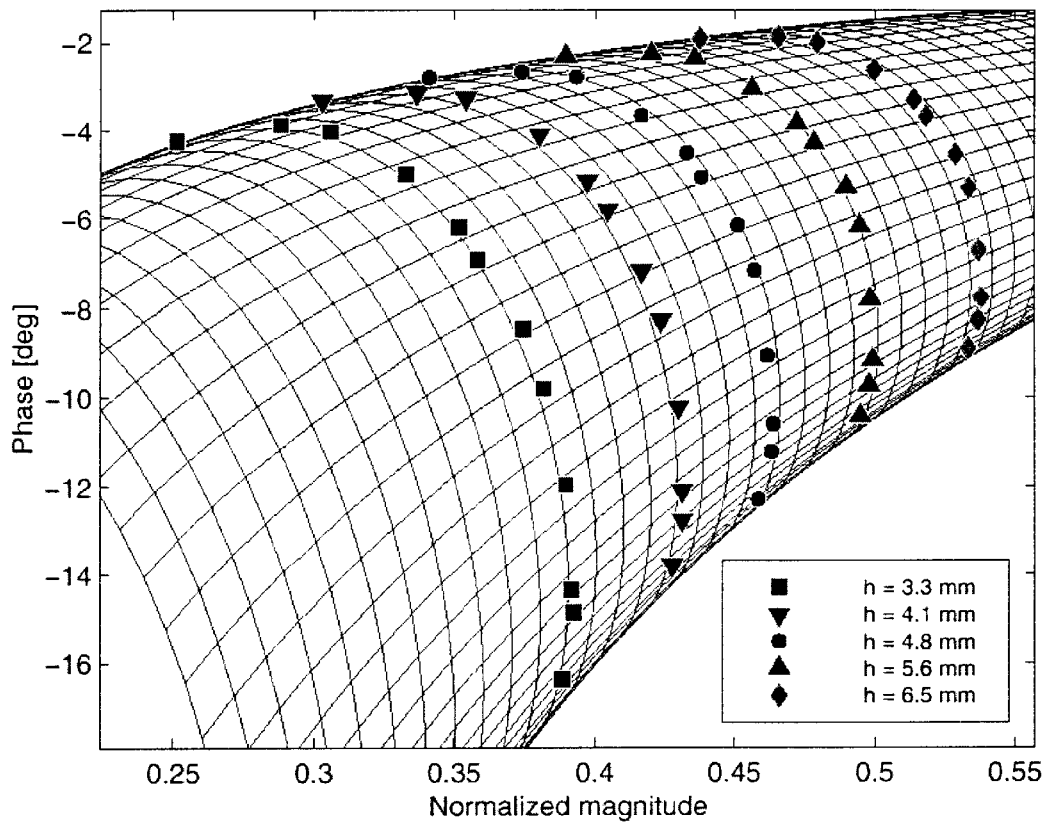
FIG. 28 shows a thickness/lift-off measurement grid for the circular magnetometer at 12.6 kHz.
Figure 29:
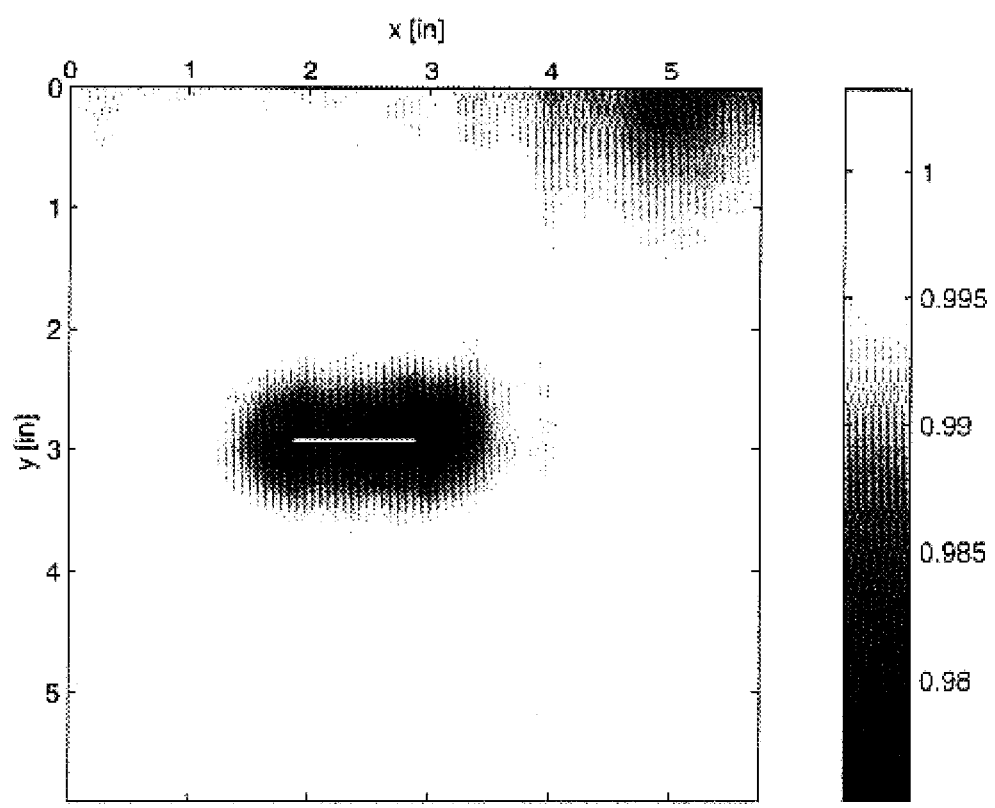
FIG. 29 is an area scan image of a stainless steel plate with a simulated crack 3.2 mm below the surface.

Measurements with a prototype GMR sensor of FIG. 27, having a diameter of about 11 inches (27.9 cm), indicate both a sensitivity to layer thickness variations at low frequency, even DC, and the capability to detect and image deeply hidden flaws. FIG. 28 shows a thickness/lift-off measurement grid and data obtained for a stainless steel 304 layer on a copper substrate. The thickness of the stainless steel layer was varied between 0.0 mm and 5.0 mm by stacking up to four plates of various thickness in different combinations. The copper plate was 3.2 mm thick. Measurements were performed at several different lift-off values and the data follows a line of constant lift-off for each set of stainless steel plate configurations. FIG. 29 shows a representative image obtained for a simulated hidden 3.2 mm below the surface of a stainless steel sample. The double hump signature of the crack, illustrated by the very dark portions of the image at the ends of the crack, is characteristic of the effect cracks have on the signal of imposed periodicity magnetometers. The crack alters the path of the induced eddy currents in the metal, which tend to mirror the current density of the drive winding. As a result, the current disruption is greatest when the crack is directly beneath the winding nearest to the sensing element. Note that the dimensions of the simulated crack (25 mm length by 0.4 mm width by 2.4 mm depth) are relatively large because the dimensions of the prototype magnetometer were large. It is also important to note that these were absolute property measurements as the only calibration involved measuring the response of the sensor in air. The measurement grid is the calculated response of the sensor from an analytical model. The good agreement between the model and the measured response has the potential to greatly simplify calibration requirements for measurements in the field and to also provide estimates of the LOP thickness for thicknesses greater than 0.070-in. (1.8 mm).

Figure 30:
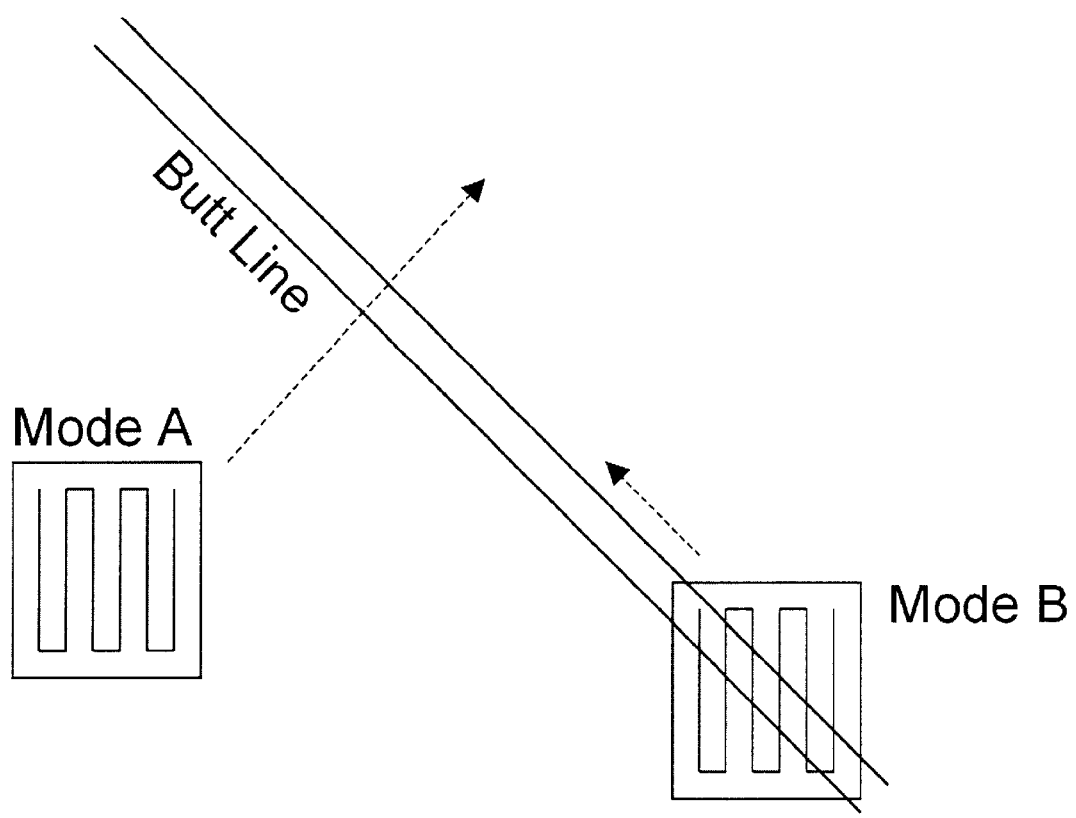
FIG. 30 is an illustration of FSW seam tracking with a single element MWM.
Figure 31:
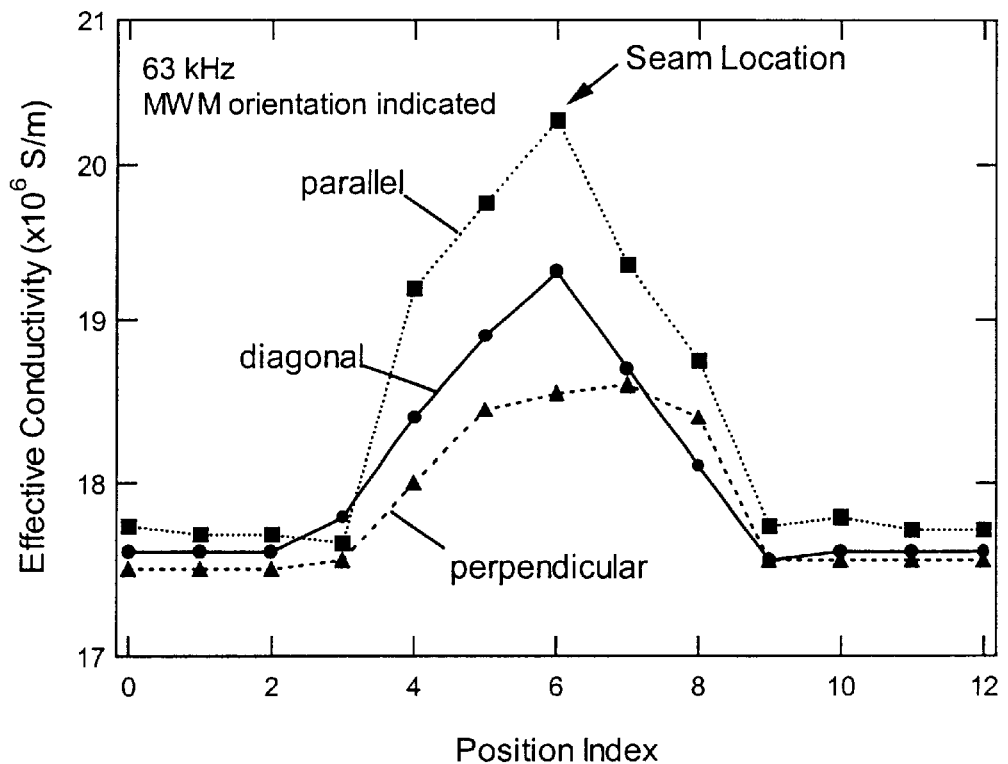
FIG. 31 is a plot of the effective conductivity of a single element MWM scanned over a weld seam at 63 kHz.
Figure 32:
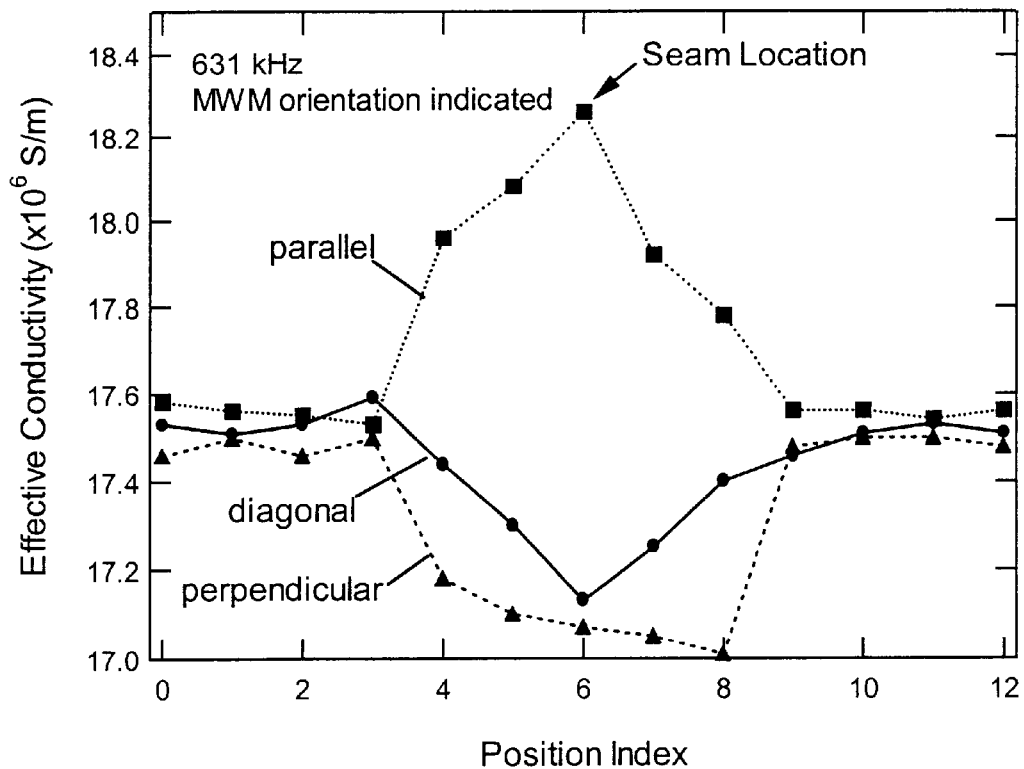
FIG. 32 is a plot of the effective conductivity of a single element MWM scanned over a weld seam at 631 kHz.

MWM sensors and MWM-Arrays can be also used in a scanning mode, i.e., with a relative movement of the material and MWM, for in-process quality control of the friction-stir welds in contact or non-contact mode as well as for seam tracking. FIG. 30 through FIG. 34 show the seam tracking capability of MWM. FIG. 30 shows two renditions of the MWM scanning seam tracking. Mode A illustrates the MWM scanning across a seam from one side to the other. Mode B illustrates a stationary MWM positioned over the seam so that it senses changes in the seam position as the material is moved by the MWM. To demonstrate the sensitivity of the MWM to the seam location, measurements were performed at two frequencies, 63 kHz and 631 kHz, as the position of the MWM relative to the seam was varied. Three orientations of the longer segments of the MWM primary winding relative to the seam axis were used: parallel, perpendicular, and diagonal (longer winding segments were at a 45 degree angle to the seam axis). Representative conductivity measurements are shown in FIG. 31 for 63 kHz and FIG. 32 for 631 kHz. The lower frequency and parallel orientation of the MWM appear to be most sensitive to the presence of the seam. As the orientation of the MWM is varied to diagonal and perpendicular, the change in the conductivity at the lower frequency is reduced, although the edges of the seam are still detected. This variation in the conductivity change with orientation of the sensor can be used to track the orientation of the seam. Furthermore, at the higher frequency, the perpendicular orientation actually has a reduction in conductivity over the seam. This implies that multiple frequency measurements can provide complementary information about the seam orientation.

Figure 33:
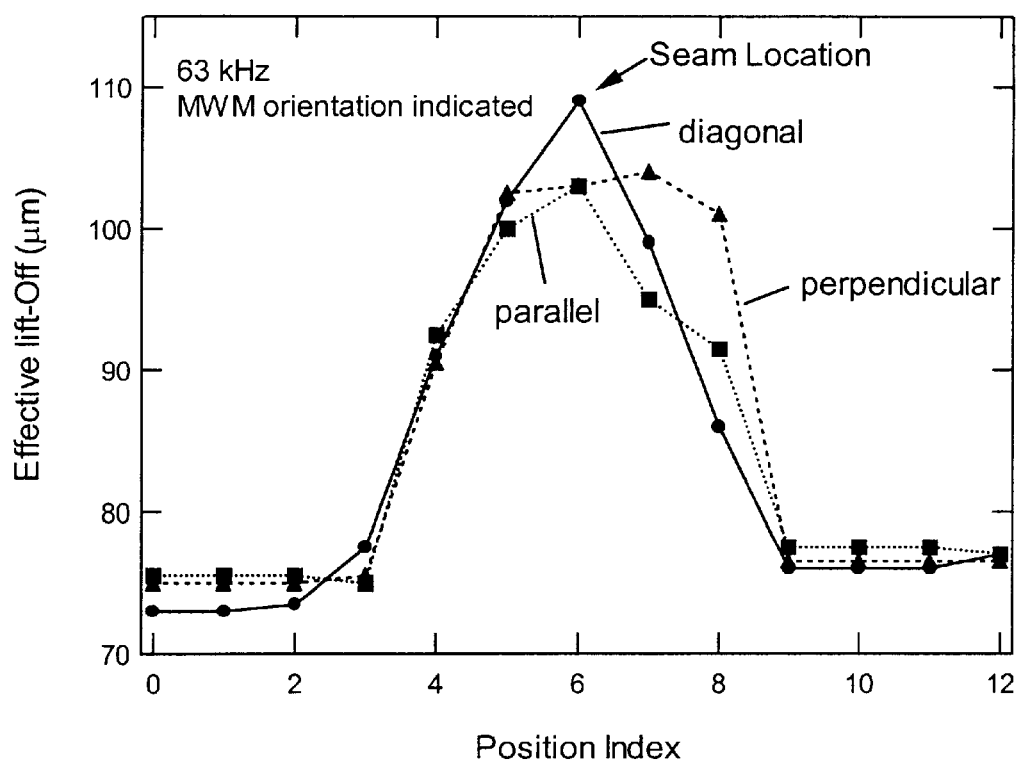
FIG. 33 is a plot of the effective lift-off of a single element MWM scanned over a weld seam at 63 kHz.
Figure 34:
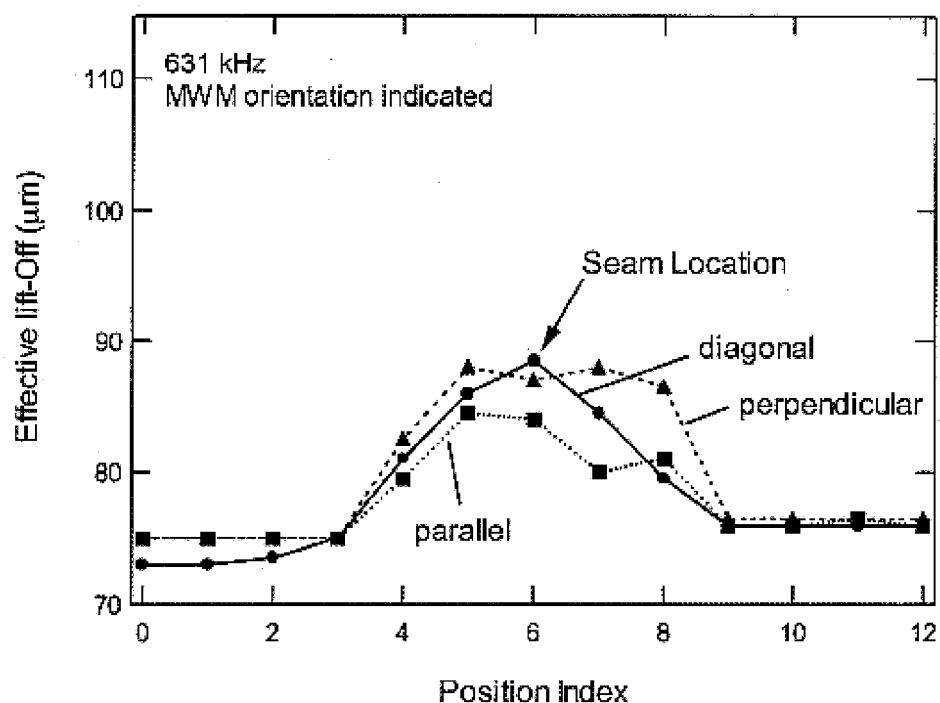
FIG. 34 is a plot of the effective lift-off of a single element MWM scanned over a weld seam at 631 kHz.

The use of grid measurement methods (described in U.S. Pat. No. 5,453,689, the entire teachings of which are incorporated herein by reference) automatically provides the lift-off information associated with each conductivity measurement. The corresponding effective lift-off response of the sensor, for each orientation is shown in FIG. 33 for 63 kHz and FIG. 34 for 631 kHz. As with the conductivity, the change in the response is largest at the lower frequencies. The relative effect of the orientation on the lift-off response is not as pronounced as the conductivity response and provides additional information about the seam orientation and location.

Figure 35:
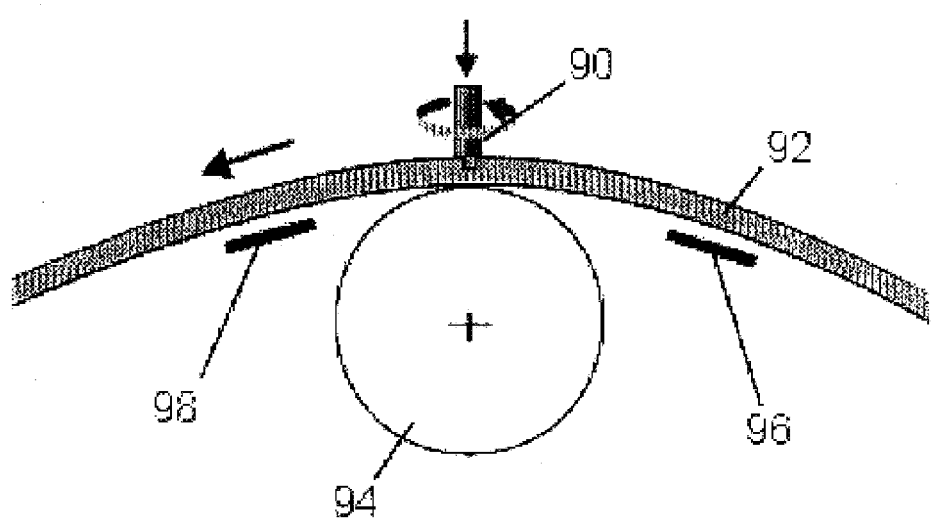
FIG. 35 is a schematic configuration for MWM sensors located before and after a weld tool.

In addition to seam tracking, where a non-contact sensor is running ahead of the weld tool, the MWM sensors and MWM-Arrays can also be used to monitor material property variations both before and after the weld tool. As an example configuration, consider FIG. 35, which has material 92 being joined by a weld tool 90 and a backside anvil 94. The MWM-Array 96 located ahead of the weld tool can be used for non-contact temperature measurement and material conductivity mapping for the purposes of alloy identification and heat treat characterization. These property variations may have an effect on the quality of the weld and the pre-weld sensor permits quality control measurements to be performed prior to the weld process. The MWM-Array 98 located after the weld tool can be used to measure temperature variations, property variations for the alloy and weld quality. Note that monitoring of these temperature variations relies on the temperature dependence of the electrical conductivity (or magnetic permeability) of the material. All of this on-line pre-weld and post-weld monitoring may be incorporated into a feedback loop for control of the process and varying weld parameters such as plunge depth, tool rotation rate, etc. to control metallurgical properties both before and after the weld tool.

It is known in the literature that conductivity mapping is an effective method of identifying plates that may have unacceptable microstructural conditions and properties due to delayed quenching, one-side quench and/or macrosegregation (Rummel, 1980). For quality control of aluminum plates at aluminum mills, quality verification of incoming plates or plates in inventory stocks, high-resolution imaging MWM-Arrays may provide not only "global" conductivity variations but also local conductivity changes for more detailed assessment of suspect local regions. The use of in-process monitoring using sensor arrays mounted in the FSW anvil or suspended before and after the FSW tool on the front and/or back side to provide in-process FSW control capability, such as the seam tracking capability illustrated in FIG. 15. For aircraft and reusable space vehicles, fatigue crack detection is also important.

Sensor constructs that incorporate magnetoresistive sensors can also be used for process quality control situations where deep penetration depths are required. For example, a magnetoresisitive sensor could be used far ahead of the weld tool (96 of FIG. 35) to determine the thickness of the plates to be welded, which could then be used as an input parameter for the weld process. Low frequencies are needed for this type of measurement, as the plate thickness can be 0.5 inches or more. In the case of ferrous alloys, high-resolution non-contact arrays can be used to measure and map the residual stress in the material. Multiple frequency measurements would allow the residual stress profile with depth to be determined as well. A magnetoresistive sensor that trails behinds the weld tool (98 of FIG. 35) could be used to perform the same residual stress mapping after the weld process. In addition, the sensor could measured both surface and deep defects, temperature variations, and may provide a control feedback mechanism for rapid cooling of the part after welding, such as quenching.

Measurements can also be performed behind the weld tool in cases where the anvil does not obstruct the entire part. The deep penetration inspection capability offered by the use of magnetoresistive sensors has the potential to replace x-ray techniques for detection and characterization of deep flaws in FSW.

While the inventions have been particularly shown and described with reference to preferred embodiments thereof, it will be understood to those skilled in the art that various changes in form and details may be made therein without departing from the spirit and scope of the invention as defined by the appended claims.

The following references are incorporated herein by reference in their entirety:

Arbegast, W. J., and Hartley, P. J. (1998), "Friction Stir Weld Technology Development at Lockheed Martin Michoud Space, Systems—An Overview", $5^{th}$ International EWI Conference on Trends in Welding Research, Jun. 1–5, 1998, Pine Mountain, Ga.

Ditzel, P., and Lippold, J. C. (1997), "Microstructure Evolution During Friction Stir Welding of Aluminum Alloy 6061-T6", Edison Welding Institute, Summary Report SR9709.

Goldfine, N. J, Clark, D., and Eckhardt, H. (1996), "Meandering Winding Test Circuit (Amended)", U.S. Pat. No. 5,793,206, Aug. 11, 1996.

Goldfine, N. J, and Melcher, J. R. (1995), "Magnetometer Having Periodic Winding Structure and Material Property Estimator," U.S. Pat. No. 5,453,689, Sep. 26, 1995.

Goldfine, N. J., Rhoads, K. G., Walrath, K. E., Clark, D. C., "Multiple Frequency Quantitative Coating Characterization," U.S. patent application Ser. No. 09/191,668, filed Nov. 13, 1998.

Goldfine, N., Schlicker, D., Sheiretov, Y., Washabaugh, A., Zilberstein, V., Lovett, T., "Conformable Eddy-Current Sensors And Arrays For Fleetwide Gas Turbine Component Quality Assessment," ASME Turbo Expo Land, Sea, & Air 2001, Jun. 4–7, 2001, New Orleans, La.

Mahoney, M. W., Rhodes, C. G., Flintoff, J. G., Spurling, R. A., and Bingel, W. H. (1998), "Properties of Friction-Stir-Welded 7075 T651 Aluminum", Metallurgical and Materials Transactions A, vol. 29A, July 1998, pp.1955–1964.

Melcher, J. R. (1991), "Apparatus and Methods for Measuring Permeability and Conductivity in Materials Using Multiple Wavenumber Magnetic Interrogations," U.S. Pat. No. 5,015,951, May 14, 1991.

Nondestructive Testing Handbook, $2^{nd}$ Edition, Volume 4: Electromagnetic Testing, American Society for Nondestructive Testing, 1986.

Rummel, W. and W. Arbegast, Proc. ASNT Spring Conf., Mar. 24–27, 1980, Philadelphia, Pa., pp.201–208.

Schlicker, D. E., Goldfine, N. J., Washabaugh, A. P., Miller, E. L. (2000), "Scalable Architecture Multi-Channel Impedance Instrument, Eddy Current Sensing Arrays, And Methods For Processing Eddy Current Sensing Arrays," U.S. Provisional Application No. 60/248,104, Nov. 13, 2000.

Schlicker, D. E., Goldfine, N. J., Washabaugh, A. P., Walrath, K. (2001), "Eddy Current Sensing Arrays," U.S. Provisional Application No. 60/276,997, Mar. 19, 2001.

The following references are also incorporated by reference in their entirety:

1. Presentation Slides titled "Autogeneous Friction Stir Weld LOP Defect Detection and Sizing Using Directional Conductivity Measurements with MWM Eddy-Current Sensor," Aeromat 2000, Seattle, Wash.
2. Presentation Slides titled "Friction Stir Weld LOP Defect Detection, Using New High Resolution MWM-Arrays and MWM Eddy-Current Sensor," Aeromat 2001, Long Beach, Calif.
3. SBIR proposal titles "High Resolution Inductive Imaging of Complex Metal Joints and Components," submitted Jun. 5, 2001.

What is claimed is:

1. A method for characterizing friction stir welds in a test material, said method comprising:

passing a time varying electric current through a sensor to form a magnetic field;

placing the sensor in proximity to the test material;

translating the sensor over a weld region;

measuring variations in an electrical property across the weld region for plural sensing element locations along the weld region; and using a feature of the electrical property measurement and location information to determine weld quality.

2. The method as claimed in claim 1 further comprising orienting extended portions of the sensor in a direction parallel to the weld axis.

3. The method as claimed in claim 1 further comprising orienting extended portions of the sensor in a direction perpendicular to the weld axis.

4. The method as claimed in claim 1 further comprising translating the sensor across the weld region, perpendicular to the weld axis.

5. The method as claimed in claim 1 further comprising translating the sensor along the weld region, parallel to the weld axis.

6. The method as claimed in claim 1 further comprising translating the sensor along a path forming a small angle with the axis of the weld region, with the extended portions of the sensor oriented perpendicular to the translation path.

7. The method as claimed in claim 6 wherein the small angle is 15 degrees.

8. The method as claimed in claim 1 wherein the electrical property is an electrical conductivity.

9. The method as claimed in claim 8 wherein the feature is a DXZ width.

10. The method as claimed in claim 8 wherein at least one sensing element measures the properties of the base material so that the response from the sensing elements is normalized by the response from the base material.

11. The method as claimed in claim 8 wherein the feature is the shape of the conductivity response across the transition region for dissimilar materials.

12. The method as claimed in claim 8 wherein the feature is an electrical conductivity at the center of the weld region.

13. The method as claimed in claim 12 wherein the weld quality is indicated by an LOP thickness.

14. The method as claimed in claim 12 wherein the weld quality is indicated by the presence of planar flaws.

15. The method as claimed in claim 1 wherein the electrical property is a magnetic permeability.

16. The method as claimed in claim 15 wherein the permeability is used to determine weld residual stress.

17. The method as claimed in claim 1 wherein the feature characterizing the weld quality is an image of the weld region created by combining the electrical property values with the position information.

18. The method as claimed in claim 17 wherein the weld quality is indicated by the presence of planar flaws.

19. The method as claimed in claim 1 further comprising the use of multiple excitation frequencies.

20. The method as claimed in claim 19 wherein the excitation frequency ranges from 100 Hz to 10 MHZ.

21. The method as claimed in claim 19 further comprising the use of pre-computed databases of the sensor response to determine several material properties simultaneously.

22. The method as claimed in claim 21 wherein the material properties are a LOP conductivity and a LOP defect thickness.

23. The method as claimed in claim 19 further comprising the use of non-linear least-square minimization calculation which minimizes the error between a predicted sensor response and the measurement data to determine several material properties simultaneously.

24. The method as claimed in claim 23 wherein the material properties are a LOP conductivity and a LOP defect thickness.

25. The method as claimed in claim 1 wherein the sensing elements are rows of inductive coils with the rows oriented parallel to the extended portions.

26. The method as claimed in claim 1 wherein sensing elements of the sensor are magnetoresistive sensors.

27. The method as claimed in claim 26 wherein the magnetoresistive sensors are in rows oriented parallel to the extended portions.

28. The method as claimed in claim 27 wherein the feature characterizing the weld quality is a high-resolution image of surface and through thickness properties of the weld region created by combining the electrical property values with the position information.

29. The method as claimed in claim 28 wherein the weld quality is indicated by the presence of a crack-like defect.

30. The method as claimed in claim 28 wherein the weld quality is indicated by a LOP defect.

31. The method as claimed in claim 30 wherein the sensor is translated over the top surface of the weld so that the LOP defect is on the opposite side of the weld.

32. The method as claimed in claim 28 wherein the weld quality is indicated by the presence of an internal flaw.

33. The method as claimed in claim 26 wherein the sensing elements have a secondary coil surrounding the magnetoresistive sensors.

34. The method as claimed in claim 33 wherein the secondary coils are used in a feedback configuration.

35. A method for characterizing friction stir welds in materials comprising:

measuring an electrical property for plural sensing element locations, including at least one location near the center of a weld and at least one location that provides the electrical property away from the center of a weld region; and using the electrical property measurements at said locations to determine weld quality.

36. The method as claimed in claim 35 where at least one sensing element of the sensor is a row of coils oriented parallel to the extended portions.

37. The method as claimed in claim 36 further comprising orienting primary extended portions of the sensor in a direction parallel to the weld axis and translating the sensor across the weld region perpendicular to the weld axis.

38. The method as claimed in claim 36 further comprising orienting primary extended portions of the sensor in a direction perpendicular to the weld axis and translating the sensor along the weld region parallel to the weld axis.

39. The method as claimed in claim 35 wherein the electrical property is an electrical conductivity.

40. The method as claimed in claim 39 wherein the electrical conductivity is used to estimate weld width.

41. The method as claimed in claim 40 wherein the weld width is used to estimate LOP depth.

42. The method as claimed in claim 39 wherein a reduction in electrical conductivity at the seam indicates a planar flaw.

43. The method as claimed in claim 35, further comprising:

placing at least two sensing elements over the weld region between two base materials.

44. The method as claimed in claim 35 further comprising:

translating a sensor over the weld region between two base materials.

* * * * *